(12) United States Patent
Yu et al.

(10) Patent No.: US 12,359,163 B2
(45) Date of Patent: *Jul. 15, 2025

(54) BACTERIAL CULTURES AND METHODS FOR PRODUCTION OF ALGINATE

(71) Applicant: Marshall University Research Corporation, Huntington, WV (US)

(72) Inventors: Hongwei D. Yu, Huntington, WV (US); Meagan E. Valentine, Huntington, WV (US); Richard M. Niles, Huntington, WV (US); Thomas Ryan Withers, Huntington, WV (US); Brandon D. Kirby, Huntington, WV (US)

(73) Assignee: Marshall University Research Corporation, Huntington, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/524,494

(22) Filed: Nov. 30, 2023

(65) Prior Publication Data

US 2024/0117300 A1   Apr. 11, 2024

Related U.S. Application Data

(63) Continuation of application No. 16/980,198, filed as application No. PCT/US2019/022330 on Mar. 14, 2019, now Pat. No. 11,873,477.

(60) Provisional application No. 62/642,772, filed on Mar. 14, 2018.

(51) Int. Cl.
  *C12N 1/20*   (2006.01)
  *C08L 5/04*   (2006.01)
  *C12R 1/38*   (2006.01)

(52) U.S. Cl.
  CPC ............... *C12N 1/205* (2021.05); *C08L 5/04* (2013.01); *C12N 1/20* (2013.01); *C12R 2001/38* (2021.05)

(58) Field of Classification Search
  CPC . C12N 1/205; C12N 1/20; C12N 1/36; C12N 9/1007; C12N 9/1051; C12N 9/1092; C12N 9/16; C08L 5/04; C12R 2001/38; C07K 14/21; C12P 19/04
  See application file for complete search history.

(56) References Cited

U.S. PATENT DOCUMENTS

2011/0184157 A1* 7/2011 Yu et al. ........... C12N 1/21 536/3
2015/0368696 A1* 12/2015 Ozanich et al. ....... C12Q 1/689

* cited by examiner

*Primary Examiner* — Satyendra K Singh
(74) *Attorney, Agent, or Firm* — Stites & Harbison, PLLC; Terry L. Wright

(57) ABSTRACT

Bacterial cultures are provided that comprise a modified *Pseudomonas aeruginosa* bacterium missing or deficient in two or more virulence factors. The two or more virulence factors can be selected from exotoxin A, hemolytic phospholipase C, phenazine-specific methyltransferase, alpha-1, 3-rhamnosyltransferase, and 3-phosphoshikimate 1-carboxyvinyltransferase. Certain of the modified *Pseudomonas aeruginosa* bacteria are also missing or deficient in one or more alginate acetylation enzymes including the alginate O-acetyltransferases AlgI, AlgJ, AlgF, AlgX, and/or the C5-mannuronan epimerase AlgG. Methods of producing alginate are also provided along with compositions comprising alginate produced by the modified *Pseudomonas aeruginosa* bacteria.

17 Claims, 16 Drawing Sheets

Specification includes a Sequence Listing.

```
SEQUENCE LISTING

Sequence total quantity: 21
SEQ ID NO: 1           moltype = DNA  length = 29
FEATURE                Location/Qualifiers
source                 1..29
                       mol_type = other DNA
                       organism = synthetic construct
SEQUENCE: 1
aattcatatt cgattgggct ggcatcagg                                    29

SEQ ID NO: 2           moltype = DNA  length = 27
FEATURE                Location/Qualifiers
source                 1..27
                       mol_type = other DNA
                       organism = synthetic construct
SEQUENCE: 2
gttcgcacat tcaccactct gcaatcc                                      27

SEQ ID NO: 3           moltype = DNA  length = 21
FEATURE                Location/Qualifiers
source                 1..21
                       mol_type = other DNA
                       organism = synthetic construct
SEQUENCE: 3
cagttgctct tcctcgccag g                                            21

SEQ ID NO: 4           moltype = DNA  length = 34
FEATURE                Location/Qualifiers
source                 1..34
                       mol_type = other DNA
                       organism = synthetic construct
SEQUENCE: 4
catgaacaag tgacctttca ttcagccgac aagg                              34

SEQ ID NO: 5           moltype = DNA  length = 20
FEATURE                Location/Qualifiers
source                 1..20
                       mol_type = other DNA
                       organism = synthetic construct
SEQUENCE: 5
aactggcgca ggcggagacc                                              20

SEQ ID NO: 6           moltype = DNA  length = 30
FEATURE                Location/Qualifiers
source                 1..30
                       mol_type = other DNA
                       organism = synthetic construct
SEQUENCE: 6
ggattgctaa gctgatgctt cctgcaatgc                                   30

SEQ ID NO: 7           moltype = DNA  length = 22
FEATURE                Location/Qualifiers
source                 1..22
                       mol_type = other DNA
```

-continued

```
                        organism = synthetic construct
SEQUENCE: 7
agccgttctg ctagcctcga cc                                              22

SEQ ID NO: 8            moltype = DNA  length = 26
FEATURE                 Location/Qualifiers
source                  1..26
                        mol_type = other DNA
                        organism = synthetic construct
SEQUENCE: 8
tgagagtagc agccgaaaag agctgg                                          26

SEQ ID NO: 9            moltype = DNA  length = 24
FEATURE                 Location/Qualifiers
source                  1..24
                        mol_type = other DNA
                        organism = synthetic construct
SEQUENCE: 9
gcgaacgcca acagccgata aagc                                            24

SEQ ID NO: 10           moltype = DNA  length = 22
FEATURE                 Location/Qualifiers
source                  1..22
                        mol_type = other DNA
                        organism = synthetic construct
SEQUENCE: 10
atctggctcg cgatgccggt cc                                              22

SEQ ID NO: 11           moltype = DNA  length = 21
FEATURE                 Location/Qualifiers
source                  1..21
                        mol_type = other DNA
                        organism = synthetic construct
SEQUENCE: 11
cgacctgaat ggttgacgct c                                               21

SEQ ID NO: 12           moltype = DNA  length = 23
FEATURE                 Location/Qualifiers
source                  1..23
                        mol_type = other DNA
                        organism = synthetic construct
SEQUENCE: 12
aagcgatgcg tctgtctagg gat                                             23

SEQ ID NO: 13           moltype = DNA  length = 21
FEATURE                 Location/Qualifiers
source                  1..21
                        mol_type = other DNA
                        organism = synthetic construct
SEQUENCE: 13
gccccaaggg ctgggtgatc g                                               21

SEQ ID NO: 14           moltype = DNA  length = 19
FEATURE                 Location/Qualifiers
source                  1..19
                        mol_type = other DNA
                        organism = synthetic construct
SEQUENCE: 14
gcgcacgcgg atgccgtgg                                                  19

SEQ ID NO: 15           moltype = DNA  length = 46
FEATURE                 Location/Qualifiers
source                  1..46
                        mol_type = other DNA
                        organism = Pseudomonas aeruginosa
SEQUENCE: 15
gccggccggt cgcggcagtt acatcgcgat ggctcctttg atgggt                    46

SEQ ID NO: 16           moltype = DNA  length = 46
FEATURE                 Location/Qualifiers
source                  1..46
                        mol_type = other DNA
                        organism = Pseudomonas aeruginosa
SEQUENCE: 16
cgcgatggac tcctcgcttc aggtcgctgc ttcggtcatc gtttat                    46

SEQ ID NO: 17           moltype = DNA  length = 47
FEATURE                 Location/Qualifiers
source                  1..47
```

```
                            mol_type = other DNA
                            organism = Pseudomonas aeruginosa
SEQUENCE: 17
aacgagagag aataaaagat gaatagggcc tgaatcggaa ctttcaa                47

SEQ ID NO: 18               moltype = DNA   length = 46
FEATURE                     Location/Qualifiers
source                      1..46
                            mol_type = other DNA
                            organism = Pseudomonas aeruginosa
SEQUENCE: 18
acaggtaagg ttgtagtttc gccgatatcg ccgcactcaa ggcgcg                 46

SEQ ID NO: 19               moltype = DNA   length = 47
FEATURE                     Location/Qualifiers
source                      1..47
                            mol_type = other DNA
                            organism = Pseudomonas aeruginosa
SEQUENCE: 19
cagcgccgtt catcaattgt tctccacgac ctcagtcatg cgccagc                47

SEQ ID NO: 20               moltype = DNA   length = 169
FEATURE                     Location/Qualifiers
source                      1..169
                            mol_type = other DNA
                            organism = Pseudomonas aeruginosa
SEQUENCE: 20
aattcatatt cgattgggct ggcatcagga aaacctgatg tatggccagg ccccgagaag  60
gccggctcct gcgaagggag ccggccggtc gcggcagtta catcgcgatg gctcctttga  120
tgggtgaagg atgaggctga tcgagcggtt ggttttttctt gtcgggcga             169

SEQ ID NO: 21               moltype = DNA   length = 115
FEATURE                     Location/Qualifiers
source                      1..115
                            mol_type = other DNA
                            organism = Pseudomonas aeruginosa
SEQUENCE: 21
gccggcggag agcggcgggg cgtctagggt gcgggttgcg gggaggctgg cggggagcgg  60
aagagagctt ttatgggatt tatgaactgg attgcagagt ggtgaatgtg cgaac       115
```

BACTERIAL CULTURES AND METHODS FOR PRODUCTION OF ALGINATE

RELATED APPLICATIONS

This application claims priority from U.S. application Ser. No. 16/980,198, filed Sep. 11, 2020, which is a 35 U.S.C. § 371 National Stage Entry of International Application No. PCT/US2019/022330, filed Mar. 14, 2019, and claiming priority to U.S. Provisional Application Ser. No. 62/642,772, filed Mar. 14, 2018, the entire disclosure of which is incorporated herein by this reference.

GOVERNMENT INTEREST

This invention was made with government support under grant number R44GM113545 awarded by the National Institutes of Health. The government has certain rights in the invention.

TECHNICAL FIELD

The presently-disclosed subject matter relates to bacterial cultures and methods for production of alginate. In particular, certain embodiments of the presently-disclosed subject matter relate to bacterial cultures including non-toxic strains of *Pseudomonas aeruginosa* and the use of those strains for the production of alginate.

BACKGROUND

Alginate is a commercially important biopolymer produced by brown seaweed and some species of bacteria. The polymer is a polysaccharide composed of the uronic acid stereoisomers, namely α-L-guluronic acid (G) and β-D-mannuronic acid (M). The relative abundance and distribution, as well as chemical modification of those monomers determine the physical characteristics of the polymer. For example, regions enriched with repeating G residues (G-blocks) result in a more rigid alginate structure, while alginate polymers with an abundance of M residues (M-blocks) have a more flexible structure, and acetylation of M monomers increases fluid absorption by the polymer. In this regard, the industrial utility of alginate is primarily due to its biocompatibility and its ability to form sodium and calcium gels.

Alginate is also a common additive to foods and cosmetics, often used as a gelling agent, and has many applications in the medical industry as well. For example, alginate hydrogels are used in advanced wound care dressings to absorb fluid, providing a moist environment to decrease infection risk and speed up wound closure. Alginate is also used as an excipient for tablets and is a common bio-ink used to form biocompatible, non-immunogenic frameworks for the 3D printing of tissues and organs. New studies are highlighting exciting new health benefits of alginate, especially for its antioxidant and anti-inflammatory properties. For example, a recent study in osteoporosis patients with degenerative lumbar disease showed that oral administration of alginate nanoparticles after corrective surgery increased antioxidant and anti-inflammatory agents such as superoxide dismutase (SOD) and interleukin-1 receptor antagonist (IL-1ra) while decreasing markers of inflammation and oxidative stress such as alanine aminotransferase (ALT) and interleukin 1β (IL-1β). Additionally, oral administration of alginate devoid of G residues (polymannuronic acid) to mice counteracted the inflammatory and obesogenic effects of a high-fat, high-sucrose diet, possibly through modulating the composition of the gut microbiota.

Currently, all alginate used commercially is extracted from brown seaweed. However, increases in ocean temperature and $CO_2$ levels as a result of climate change is a looming threat to seaweed habitats and alginate yields. While laboratory cultivation of brown seaweed is possible, it is expensive. Additionally, the ability to tailor the composition of seaweed alginate to suit specific applications is limited.

The only other known sources of alginate are from cultures of bacterial species of the genera *Azotobacter* and *Pseudomonas*. Among these bacteria, alginate biosynthesis has been best studied in *Pseudomonas aeruginosa*. *P. aeruginosa* is a ubiquitous Gram-negative bacterium found in soil, water, and man-made environments. However, it is also an opportunistic pathogen that can cause life-threatening infections in immunocompromised patients, including those with respiratory infections, urinary tract infections, bacteremia, and underlying disease such as cystic fibrosis. Indeed, *P. aeruginosa* has a large genome and harbors genes for the production of many secreted virulence factors, including proteases, exoenzymes, exotoxins, and lipases. In addition to secreted toxins, the cell envelope of *P. aeruginosa* also contains virulence factors such as flagella, adhesins, and lipopolysaccharide (LPS) in its outer membrane. *P. aeruginosa* is also capable of forming biofilms that protect the organism from environmental stressors, including dehydration, predation, antibiotics, and host defenses. It is appreciated that the *P. aeruginosa* biofilm is rich in alginate, but extracting and using alginate produced by *P. aeruginosa* is also generally problematic not only due to the potential pathogenicity of the organism, but also the low and inconsistent alginate yields that have previously been exhibited by wild-type strains. Thus, there is currently a growing and unmet need for more reliable and customizable sources of alginate.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes bacterial cultures and methods for production of alginate. In particular, certain embodiments of the presently-disclosed subject matter include bacterial cultures including non-toxic strains of *Pseudomonas aeruginosa* and the use of those strains for the production of alginate. In some embodiments, a bacterial culture is provided that comprises a modified *Pseudomonas aeruginosa* bacterium missing or deficient in two or more virulence factors. In some embodiments, the two or more virulence factors are selected from exotoxin A, hemolytic phospholipase C, phenazine-specific methyltransferase, alpha-1,3-rhamnosyltransferase, 3-phosphoshikimate 1-carboxyvinyltransferase, and combinations thereof. For example, in certain embodiments, the modified *Pseudomonas aeruginosa* bacterium is missing or deficient in a combination of exotoxin A, hemolytic phospholipase C, phenazine-specific methyltransferase, alpha-1,3-rhamnosyltransferase, and 3-phosphoshikimate 1-carboxyvinyltransferase.

To produce a modified *Pseudomonas aeruginosa* bacterium missing or deficient in various virulence factors, in some embodiments, the modified *Pseudomonas aeruginosa* bacterium includes a deletion of two or more virulence factor genes, where the virulence factor genes are selected from toxA, plcH, phzM, wapR, aroA, and combinations thereof.

In some embodiments, and in addition to the missing or deficient virulence factors, the modified *Pseudomonas aeruginosa* bacterium is missing or deficient in one or more alginate acetylation enzymes. In some embodiments, the one or more alginate acetylation enzymes are selected from the group consisting of alginate O-acetyltransferase AlgI, alginate O-acetyltransferase AlgJ, alginate O-acetyltransferase AlgF, and alginate O-acetyltransferase AlgX. In some embodiments, the modified *Pseudomonas aeruginosa* bacterium is missing or deficient in alginate O-acetyltransferase AlgI and alginate O-acetyltransferase AlgJ. In some embodiments, to produce such a modified *Pseudomonas aeruginosa* bacterium, the modified *Pseudomonas aeruginosa* bacterium includes a deletion of one or more alginate acetylation genes, where the alginate acetylation genes are selected from algI, algJ, algF, and algX.

In some embodiments, the modified *Pseudomonas aeruginosa* bacterium described herein further include one or more modifications to alter the composition of the alginate produced by the bacterium. For example, in some embodiments, the modified *Pseudomonas aeruginosa* bacterium includes an algG gene having one or more mutations such that the algG gene encodes an AlgG protein having decreased C5-mannuronan epimerase activity as compared to wild-type *Pseudomonas aeruginosa* bacteria but still provides the scaffold required for the transport of alginate polymer across the periplasm, and such that the modified *Pseudomonas aeruginosa* bacterium produces alginate comprised of only M units (i.e., a polyM alginate).

Further provided, in some embodiments of the presently-disclosed subject matter, are methods for producing alginate. In some embodiments, a method of producing alginate is provided that comprises the step of culturing a modified *Pseudomonas aeruginosa* bacterium of the presently-disclosed subject matter and subsequently isolating the alginate produced by the modified *Pseudomonas aeruginosa* bacterium. In some embodiments, to facilitate the production of alginate, the modified *Pseudomonas aeruginosa* bacterium is transformed with a plasmid or other vector encoding a MucE polypeptide, where the MucE polypeptide is expressed from the plasmid or vector. In some embodiments, the alginate produced by the modified *Pseudomonas aeruginosa* bacterium is non-acetylated. In some embodiments, the produced alginate is comprised of only M subunits.

Still further provided, in some embodiments, are compositions that comprise alginate produced by the modified *Pseudomonas aeruginosa* bacterium described herein.

Further features and advantages of the present invention will become evident to those of ordinary skill in the art after a study of the description, figures, and non-limiting examples in this document.

BRIEF DESCRIPTION OF THE DRAWINGS

FIG. 2A is a western blot analysis of Exotoxin A from Exotoxin A-positive *P. aeruginosa* PA103, wild-type *P. aeruginosa* PAO1, and PGN5 culture medium. PM was used as a negative control. Arrow indicates absence of Exotoxin A signal from PGN5 culture medium. FIG. 2B is an image showing hemolysis on blood agar observed with *P. aeruginosa* strains PAO1 and VE2, but not PGN5 or *E. coli* strain BL21. Areas of β-hemolysis shown with white arrows. FIG. 2C is a graph showing pyocyanin concentrations in PAO1 and PGN5 media. FIG. 2D includes images showing silver stained SDS-PAGE (left) and Western blot analysis (right) against O-antigen on cell lysates of *P. aeruginosa* strains PAO1$_{wbpL}$, PAO1 VE2, and PGN4. O-antigen regions boxed in red. Antibodies used are indicated. Arrow indicates reduced O-antigen detected in PGN4 strain. FIG. 2E is a graph showing the results of an ELISA of cell lysates of PAO1 and PGN5 for 3-phosphoshikimate 1-carboxyvinyltransferase (AroA). ***$p<0.001$, determined by two-tailed Student's t-test.

FIG. 3A is an image showing the non-mucoid phenotype of *P. aeruginosa* strains PAO1 and PGN5 on PIA. FIG. 3B is an image showing mucoid phenotype of PGN5+mucE and VE2 on PIAGm300. FIG. 3C is a graph showing the results of a uronic acid (carbazole) assay used to measure alginate production on VE2 and PGN5+mucE over a 3-day period. FIG. 3D is a graph showing an overlay of HPLC chromatograms on alginate prepared from *P. aeruginosa* strains VE2 (red) and PGN5+mucE (blue). Only area of interest is shown. X axis=retention time; Y axis=absorbance units. FIG. 3E is a graph showing measured viscosity of 2% sodium alginate gels prepared from alginate produced by VE2 and PGN5+mucE. FIG. 3F is a graph showing an overlay of shear stress/shear rate measured from 2% sodium alginate gels prepared from alginate produced by VE2 (red) and PGN5+mucE (blue).

FIG. 4A is a graph showing percent survival of male mice, n=10. FIG. 4B is a graph showing percent survival of female mice, n=10. FIG. 4C is a graph showing percent survival of combined survival of both male and female, n=20.

BRIEF DESCRIPTION OF THE SEQUENCE LISTING

Figure 1:
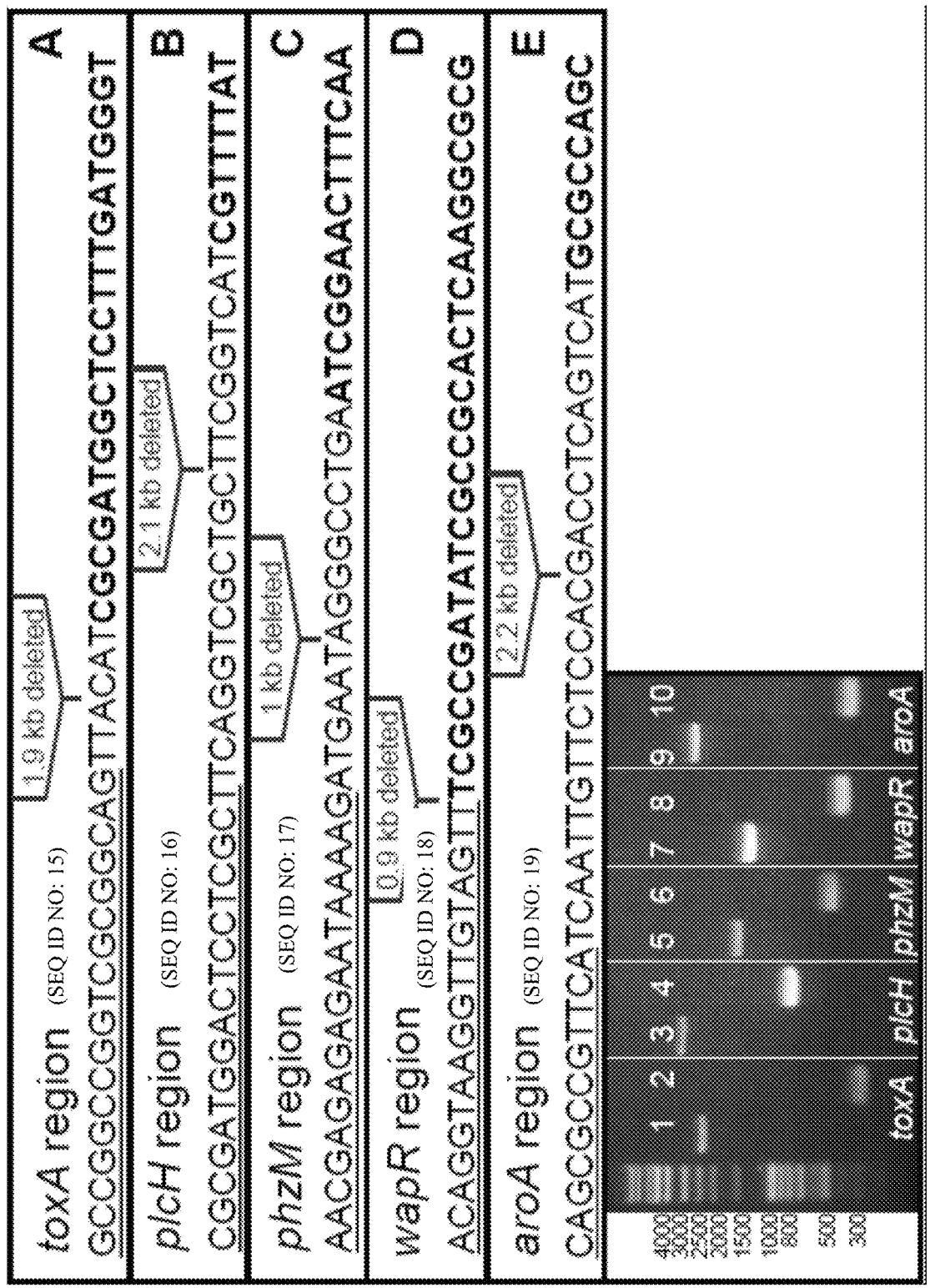
FIG. 1 is a diagram and image showing confirmation of deletion of five gene sequences in *P. aeruginosa* strain PGN5. Panels A-E show Sanger sequencing results of each gene deletion in the PGN5 strain. Panels A, B, and E show plus strand sequence obtained. Panels C and D show minus strand sequence obtained. Underlined sequence is upstream of the start codon of each gene. Bold sequence is downstream of the stop codon of each gene. Location of deleted sequence is shown by brackets. The lower image shows an agarose gel electrophoresis from PCR amplification of deleted gene regions. Odd lanes are PCR products from *P. aeruginosa* strain PAO1, even lanes are PCR products from strain PGN5.

SEQ ID NO: 1 is the nucleic acid sequence of a forward primer used to confirm the in frame deletion of a toxA gene.

SEQ ID NO: 2 is the nucleic acid sequence of a reverse primer used to confirm the in frame deletion of a toxA gene.

SEQ ID NO: 3 is the nucleic acid sequence of a forward primer used to confirm the in frame deletion of a plcH gene.

SEQ ID NO: 4 is the nucleic acid sequence of a reverse primer used to confirm the in frame deletion of a plcH gene.

SEQ ID NO: 5 is the nucleic acid sequence of a forward primer used to confirm the in frame deletion of a phzM gene.

SEQ ID NO: 6 is the nucleic acid sequence of a reverse primer used to confirm the in frame deletion of a phzM gene.

SEQ ID NO: 7 is the nucleic acid sequence of a forward primer used to confirm the in frame deletion of a wapR gene.

SEQ ID NO: 8 is the nucleic acid sequence of a reverse primer used to confirm the in frame deletion of a wapR gene SEQ ID NO: 9 is the nucleic acid sequence of a forward primer used to confirm the in frame deletion of an aroA gene.

SEQ ID NO: 10 is the nucleic acid sequence of a reverse primer used to confirm the in frame deletion of an aroA gene.

SEQ ID NO: 11 is the nucleic acid sequence of a forward primer used to confirm the in frame deletion of an algI/J gene.

SEQ ID NO: 12 is the nucleic acid sequence of a reverse primer used to confirm the in frame deletion of an algI/J gene.

SEQ ID NO: 13 is the nucleic acid sequence of a forward primer used to confirm the in frame deletion of an algG gene.

SEQ ID NO: 14 is the nucleic acid sequence of a reverse primer used to confirm the in frame deletion of an algG gene.

SEQ ID NO: 15 is a nucleic acid sequence showing confirmation of toxA gene deletion in *Pseudomonas aeruginosa*.

SEQ ID NO: 16 is a nucleic acid sequence showing confirmation of plcH gene deletion in *Pseudomonas aeruginosa*.

SEQ ID NO: 17 is a nucleic acid sequence showing confirmation of phzM gene deletion in *Pseudomonas aeruginosa*.

SEQ ID NO: 18 is a nucleic acid sequence showing confirmation of wapR gene deletion in *Pseudomonas aeruginosa*.

SEQ ID NO: 19 is a nucleic acid sequence showing confirmation of aroA gene deletion in *Pseudomonas aeruginosa*.

SEQ ID NO: 20 is a nucleic acid sequence showing confirmation of toxA gene deletion in *Pseudomonas aeruginosa* and showing sequencing upstream of toxA.

SEQ ID NO: 21 is a nucleic acid sequence showing confirmation of toxA gene deletion in *Pseudomonas aeruginosa* and showing sequencing downstream of toxA.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is based, at least in part, on the development of a bacterial culture comprising a nonpathogenic strain of *Pseudomonas aeruginosa* through the sequential deletion of five virulence factor genes from the chromosome of a wild-type *P. aeruginosa* strain. In particular, it was surprisingly found that the modified *Pseudomonas aeruginosa* was non-pathogenic, but yet was capable of producing large quantities of alginate upon deliberate activation of the alginate biosynthetic pathway and that the produced alginate was similar to that of wild-type *P. aeruginosa*. In this regard, the modified *Pseudomonas aeruginosa* provided a suitable alternative to seaweed for producing alginate that was safe for human use and, without being bound by any particular theory or mechanism, that was thought to be capable of providing a reliable source of alginates and other recombinant proteins with specific physical properties so as to suit different industrial and biomedical needs.

The presently-disclosed subject matter thus includes bacterial cultures and methods for production of alginate. In particular, certain embodiments of the presently-disclosed subject matter relate to bacterial cultures including non-toxic strains of *Pseudomonas aeruginosa* and the use of those strains for the production of alginate.

In some embodiments of the presently-disclosed subject matter, a bacterial culture is provided that comprises a modified *Pseudomonas aeruginosa* bacterium that is missing or deficient in two or more virulence factors naturally found in the bacterium. The term "virulence factor" is used herein to refer to molecules, such as polypeptides, that are produced by bacteria, as well as viruses, fungi, and protozoa, and which enable those organisms to achieve certain functions including, but not limited to, the ability of those organisms to achieve colonization in a particular host such as by attachment to the cells of the host, to evade or inhibit a host's immune response, to gain entry into and exit from the cells of the host, and/or to obtain nutrition from the host. Such virulence factors can vary widely depending on the particular organism and each particular organism can include a wide array of virulence factors from a variety of different sources. In bacteria, for example, such virulence factors can include factors that assist and promote colonization of the host, such as adhesins, invasins, and antiphagocytic factors, as well as factors that damage the host, either directly or indirectly, such as toxins, hemolysins, and proteases. Such virulence factors can be chromosomally encoded and intrinsic to the bacteria (e.g. capsules and endotoxin), while other virulence factors in bacteria can be obtained from mobile genetic elements like plasmids and bacteriophages (e.g. some exotoxins).

In some embodiments, the virulence factors missing or deficient in the modified *Pseudomonas aeruginosa* bacterium of the presently-disclosed subject matter are polypeptides selected from: exotoxin A (GenBank reference AAG04537.1), which inhibits protein synthesis in the host by deactivating elongation factor 2 (EF-2); hemolytic phospholipase C (GenBank reference AAG04233.1), which acts as a surfactant and damages host cell membranes; phenazine-specific methyltransferase (GenBank reference AAG07596.1), which is an enzyme required for the production of the redox active, pro-inflammatory, blue-green secreted pigment, pyocyanin; alpha-1,3-rhamnosyltransferase (GenBank reference AAG08385.1), which is involved in synthesizing O-antigen, a component of lipopolysaccharide (LPS) of the outer membrane of the *Pseudomonas* organism; and 3-phosphoshikimate 1-carboxyvinyltransferase (GenBank reference AE004091.2), which is required intracellularly for aromatic amino acid synthesis; and combinations thereof.

In some embodiments, the modified *Pseudomonas aeruginosa* bacteria are missing or deficient in at least one of the foregoing virulence factors, while, in other embodiments, the modified *Pseudomonas aeruginosa* bacteria are missing or are deficient in two or more of the foregoing virulence factors. In some embodiments, such modified bacteria that are missing or deficient in two or more of the virulence factors are generated via the sequential deletion of the genes encoding the virulence factors. For instance, in some embodiments, a modified *Pseudomonas aeruginosa* bacterium is provided that is missing or deficient in only exotoxin A and is referred to herein as PGN1. In another embodiment, the modified *Pseudomonas aeruginosa* bacterium that is missing or deficient in exotoxin A is further modified such that it is missing or deficient in hemolytic phospholipase C as well and is referred to herein as PGN2. That bacterium, in further embodiments, is then modified to be missing or deficient in phenazine—specific methyltransferase and is referred to herein as PGN3. In yet further embodiments, the PGN3 bacterium is then additionally modified such that it is missing or deficient in four virulence factors, namely exotoxin A, hemolytic phospholipase C, phenazine-specific methyltransferase, and alpha-1,3-rhamnosyltransferase, and is referred to herein as PGN4. Even further, in other embodiments, a modified *Pseudomonas aeruginosa* bacterium is then produced that is missing or deficient in five virulence factors, exotoxin A, hemolytic phospholipase C, phenazine-specific methyltransferase, alpha-1,3-rhamnosyltransferase, and 3-phosphoshikimate 1-carboxyvinyltransferase, and is referred to herein as PGN5.

With further regard to the bacteria missing or deficient in virulence factors, the term "missing" is used herein to refer to modified *Pseudomonas aeruginosa* bacteria in which certain virulence factors are absent or otherwise incapable of detection in the bacteria, while the term "deficient" is used to refer to modified *Pseudomonas aeruginosa* bacteria in which the amount or activity level of the virulence factors is decreased as compared to the amount or activity level of the virulence factors typically found in wild-type *Pseudomonas aeruginosa* bacteria. In this regard, the term "modification" or "modified" when used in reference to a *Pseudomonas aeruginosa* bacteria of the presently-disclosed subject matter refers to a *Pseudomonas aeruginosa* bacterium in which there has been a modification of a sequence of amino acids of a polypeptide of the *Pseudomonas aeruginosa* bacteria or a sequence of nucleotides in a nucleic acid molecule of the *Pseudomonas aeruginosa* bacteria, and can thus include deletions, insertions, and replacements of amino acids and nucleotides, respectively.

As used herein, "deletion," when referring to a nucleic acid molecule or polypeptide, refers to the deletion of one or more nucleotides from the nucleic acid molecule or deletion of one or more amino acids from the polypeptide compared to a sequence, such as a target polynucleotide or polypeptide or a native or wild-type sequence. "Insertion," on the other hand, when referring to a nucleic acid molecule or polypeptide, describes the inclusion of one or more additional nucleotides in the nucleic acid molecule or one or more amino acids in the polypeptide, within a target, native, wild-type or other related sequence. Thus, a nucleic acid molecule that contains one or more insertions compared to a wild-type sequence, contains one or more additional nucleotides within the linear length of the sequence. In some embodiments, the term "additions" is further used to describe the addition of nucleotides or amino acids onto either termini compared to another nucleic acid molecule or polypeptide.

As used herein, "substitution" or "replacement" refers to the replacing of one or more nucleotides or amino acids in a native, target, wild-type or other nucleic acid molecule or polypeptide sequence with an alternative nucleotide or amino acid, without changing the length (as described in numbers of residues) of the molecule. Thus, one or more substitutions in a molecule does not change the number of amino acid residues or nucleotides of the molecule. Substitution mutations compared to a particular polypeptide can be expressed in terms of the number of the amino acid residues along the length of the polypeptide sequence. For example, a modified polypeptide having a modification in the amino acid at the 19th position of the amino acid sequence that is a substitution of Isoleucine (Ile; I) for cysteine (Cys; C) can be expressed as I19C, Ile19C, or simply C19, to indicate that the amino acid at the modified 19th position is a cysteine. In this example, the molecule having the substitution has a modification at Ile 19 of the unmodified polypeptide.

Various methods of modifying a polypeptide or a nucleic acid (e.g., a gene of interest) are routine to those of skill in the art, such as by using recombinant DNA methodologies, direct synthesis, and the like. In some embodiments, the modification that results in a missing or deficient virulence factor includes mutations that result in alterations in protein coding sequences, e.g., mutations that result in premature termination codons and/or mutations that result in nonfunctional proteins and/or mutations that delete the gene completely. In some embodiments, the modification that results in a missing or deficient virulence factor include mutations that affect regulator sequences and reduce transcription or translation of the virulence factors themselves or other factors that regulate the transcription or translation of the virulence factors.

In some embodiments, the modification that results in a missing or deficient virulence factor includes an in frame deletion of the gene encoding a particular virulence factor. For instance, in some embodiments, to perform such in frame deletions, plasmid inserts can first be generated by PCR-amplification of a nucleotide sequence directly upstream and of a nucleotide sequence directly downstream of each gene encoding a particular virulence factor, followed by fusion of these DNA fragments via crossover PCR. The resultant PCR product can then be digested and ligated into a suitable plasmid before the plasmid carrying its specific insert is introduced into a *Pseudomonas aeruginosa* bacterium. Once the bacterium is transformed with the plasmid, the target gene can then be deleted with a two-step allelic exchange procedure whereby homologous recombination between one site on the plasmid and its target site on the chromosome of the *Pseudomonas aeruginosa* bacterium integrates the plasmid into the *P. aeruginosa* chromosome (i.e., a single-crossover event). Such single-crossovers can then be selected by plasmid-conferred resistance to an antibiotic and/or sensitivity to 10% (w/v) sucrose supplemented in PIA. Single-crossovers can then be grown overnight to allow for homologous recombination between the second site on the plasmid with its target site on the chromosome (i.e., a double-crossover event), which removes the entire plasmid sequence along with the target gene sequence. Those double-crossovers can then be selected by plasmid conferred-sensitivity, indicating that the plasmid sequence has been removed.

With further regard to the deletion of virulence genes in accordance with the presently-disclosed subject matter, in some embodiments, a modified Pseudomonas aeruginosa bacterium includes a deletion of two or more virulence factor genes. In some embodiments, such virulence factor genes are selected from: toxA (GenBank reference AAG04537.1), which encodes the secreted toxin exotoxin A; plcH (GenBank reference AAG04233.1), which encodes the secreted toxin hemolytic phospholipase C; phzM (GenBank reference AAG07596.1), which encodes phenazine-specific methyltransferase; wapR (GenBank reference AAG08385.1), which encodes the rhamnosyltransferase involved in synthesizing O-antigen; aroA (GenBank reference AE004091.2), which encodes 3-phosphoshikimate 1-carboxyvinyltransferase; and combinations thereof.

The term "gene" is used broadly herein to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated.

The term "isolated", when used in the context of an isolated nucleic acid molecule, an isolated polypeptide, or even an isolated bacterium is a nucleic acid molecule, polypeptide, or bacterium that, by the hand of man, exists apart from its native environment and is therefore not a product of nature. An isolated nucleic acid molecule or polypeptide can exist in a purified form or can exist in a non-native environment such as, for example, in a transgenic host cell (e.g., a bacterial cell).

The terms "polypeptide," "protein," and "peptide" are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

In addition to the deletion and/or modification of one or more genes encoding a Pseudomonas aeruginosa virulence factor polypeptide, in some embodiments, the modified Pseudomonas aeruginosa bacteria of the presently-disclosed subject matter are also missing or deficient in one or more alginate acetylation enzymes. Acetylation, i.e. the addition of acetyl groups, can also affect the properties of alginates. Alginate produced from brown seaweed is structurally similar to alginate isolated from bacteria of the genera Azotobacter and Pseudomonas. However, unlike seaweed alginate, bacterially produced alginates may be O-acetylated on the C-2 and C-3 carbons of D-mannuronate residues, and the degree of acetylation may vary. In Pseudomonas aeruginosa bacteria, the acetylation of alginate occurs through the combined activity of four genes encoding the periplasmic proteins, AlgI, AlgJ, AlgF, and AlgX. In this regard, in some embodiments, a modified Pseudomonas aeruginosa bacterium is provided that is missing or deficient in one or more alginate acetylation enzymes selected from alginate O-acetyltransferase AlgI (GenBank reference AAG06936.1), alginate O-acetyltransferase AlgJ (GenBank reference AAG06937.1), alginate O-acetyltransferase AlgF (GenBank reference AAG06938.1), and alginate O-acetyltransferase AlgX (GenBank reference AAG06934.1). In some embodiments, the modified Pseudomonas aeruginosa bacterium is missing or deficient in alginate O-acetyltransferase AlgI and alginate O-acetyltransferase AlgJ. In some embodiments, such modified Pseudomonas aeruginosa bacterium include a deletion of one or more alginate acetylation genes, including, in some embodiments, alginate acetylation genes selected from algI, algJ, algF, algX, and combinations thereof.

In some embodiments, and in addition to modulating the amount of acetylation present in the alginate produced by the Pseudomonas aeruginosa bacteria of the presently-disclosed subject matter, the Pseudomonas aeruginosa bacteria are further modified to produce alginates having additional, differing properties. As noted, in Pseudomonas aeruginosa bacteria, alginate is polymerized from M monomers, some of which are converted to G residues by the C5-mannuronan epimerase AlgG, typically yielding an alginate composition of about 30% G and 70% M. Alginates with varying M:G ratios, however, have different properties. For example, alginates with higher G content, especially long stretches of G residues (G-blocks), form stiffer gels. Likewise, alginates with higher M content form more fluid gel structures. In some embodiments, and in addition to providing a non-pathogenic strain of Pseudomonas aeruginosa bacteria, Pseudomonas aeruginosa bacteria are thus provided that, by modulating the presence or activity level of AlgG (or other C5-epimerases) in the Pseudomonas aeruginosa bacteria, manipulates the M:G composition of alginate typically observed in Pseudomonas aeruginosa bacteria. In some embodiments, such a modified Pseudomonas aeruginosa bacterium includes an algG gene having one or more mutations such that the algG gene encodes an AlgG polypeptide having decreased C5-mannuronan epimerase activity as compared to wild-type Pseudomonas aeruginosa bacteria. In some embodiments, such a mutation eliminates the epimerase activity of the AlgG present in the Pseudomonas aeruginosa bacteria such that an alginate can be produced including only M monomers.

Still further provided, in some embodiments, are methods of producing alginate that make use of the modified Pseudomonas aeruginosa bacteria described herein. In some embodiments, a method of producing alginate is provided that comprises culturing a modified Pseudomonas aeruginosa bacterium of the presently-disclosed subject matter and that is missing or deficient in two or more virulence factors, and then isolating the produced alginate by methods known to those skilled in the art. In some embodiments, to facilitate the activation of the alginate biosynthetic operon, which contains the genes required for alginate production, the modified *Pseudomonas aeruginosa* bacterium is further transformed with a vector which encodes an activator of the alginate operon and that leads to alginate production and a mucoid phenotype in the modified *Pseudomonas aeruginosa* bacterium. For example, in some embodiments, the modified *Pseudomonas aeruginosa* bacterium is transformed with a vector that encodes a MucE polypeptide, an activator of the alginate biosynthetic pathway, that is expressed from the vector.

The term "vector" is used herein to refer to any vehicle that is capable of transferring a nucleic acid sequence into another cell. For example, vectors which can be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art and can include vectors that integrate a nucleic acid sequence of interest into the chromosomes present in a cell as well as vectors that express a given nucleic acid sequence extrachromosomally). As one exemplary embodiment of a vector comprising a nucleic acid sequence of the presently disclosed subject matter, an exemplary vector can be a plasmid into which a nucleic acid encoding an activator of the alginate biosynthetic pathway (e.g., mucE; GenBank Reference AAG07420.1) can be cloned by the use of internal restriction sites present within the vector. For further explanation and guidance regarding MucE and the alginate biosynthetic pathway, see, e.g., U.S. Pat. Nos. 8,399,649 and 9,175,322 as well as Qiu, et al. (Proc. Natl Acad Sci USA 104(19):8107-8112), each of which are incorporated herein by reference in their entirety.

In some embodiments, such nucleic acids that are incorporated into a vector of the presently-disclosed subject matter are operably linked to an expression cassette. The terms "associated with," "operably linked," and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, an expression cassette is provided that comprises a "constitutive promoter" that continually expresses a nucleic acid sequence (e.g., a nucleic acid encoding MucE) of the presently-disclosed subject matter in all types of cells where it is inserted.

As noted, the presently-disclosed subject matter provides modified *Pseudomonas aeruginosa* bacteria as well as bacterial cultures comprising the bacteria. In some embodiments, the bacterial cultures can be liquid, for example in LB broth, or solid, for example in agarose. The bacterial cultures can also be frozen cultures, cultures in stationary phases, and/or cultures in growth phase.

Still further provided, in some embodiments of the presently-disclosed subject matter, are compositions that comprise alginate produced by the modified *Pseudomonas aeruginosa* bacteria described herein. The isolated bacterial alginate of the presently-disclosed subject matter can be used in compositions as, for example, gelling, thickening, stabilizing, swelling, and viscosity imparting agents. Thus, in some embodiments, the isolated bacterial alginate of the presently-disclosed subject matter are useful in, for example, the food, textile, dental, pharmaceutical, cosmetic, and paper industries. In some embodiments, the alginate produced by the presently-disclosed subject matter are included in compositions that serve as a thickening agent in, for example, food items, such as ice cream, salad dressing, pet food chunks, low fat spreads, sauces and pie filings. In some embodiments, the bacterial alginates can also be used in other diverse applications including for fixation and color in textile printing, for improving surface quality in paper and board treatments, for improving bendability of rods, for increasing aggregate size in flocculation processes in water treatment, for forming slits in can sealings, for concentrating latex during rubber extraction from plants, for reducing rates of surface drying in production of ceramics and foods, or for immobilization of cells.

In some embodiments, the isolated bacterial alginate of the presently-disclosed subject matter can also be incorporated into wound dressings to provide a moist surface for healing. Alginate fibers trapped in a wound are readily biodegraded. Dressings with alginate are used to treat ulcers in diabetic patients. Propylene glycol alginate has been used as an acid-stable stabilizer for uses such as preserving the white fluffy head of foam on beers. Furthermore, the bacterial alginates of the presently-disclosed subject matter can be used to sequester cations, such as iron, from solutions, and therefore can be useful in filtering systems. Alginate absorbs radioactive elements, heavy metals and free radicals. Because alginate cannot be broken down by bile or saliva and cannot be absorbed by the body, it is secreted from the body together with the heavy metals and radioactive substances.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-7

Bacterial strains, culture, plasmids, and oligonucleotides. Bacterial strains and plasmids utilized are listed in Table 1 and Table 2. *P. aeruginosa* strains were either grown on *Pseudomonas* isolation agar (PIA) plates or in *Pseudomonas* isolation broth (PIB) at 37° C. (Difco, Sparks, MD, USA). *E. coli* strains were cultured in Luria Broth (LB) or on LB with 1% agar at 37° C. (Difco, Sparks, MD, USA). When necessary, plates were supplemented with the following antibiotics: gentamicin or carbenicillin at a concentration of 300 μg/mL for *P. aeruginosa* and 30 μg/mL for *E. coli*; kanamycin at a concentration of 50 μg/mL for *E. coli*. PGN5 was grown on a medium supplemented with 1 mg/mL of the aromatic amino acids (Y, W, F) unless otherwise stated.

TABLE 1

Strains used.

| Strain | Genotype | Relevant Characteristics | Source |
|---|---|---|---|
| *Pseudomonas aeruginosa* strains | | | |
| PAO1 | Wild-type serogroup O5 | Non-mucoid, blue-green growth on PIA | (Kropinski, et al. 1979) |
| VE2 | PAO1 with chromosomal fusion of $P_{Gm}$-aacC1-mucE | Mucoid, blue-green growth on PIA | (Qiu, et al. 2007) |
| PA-103 | Serogroup O11 | Positive for Exotoxin A secretion | (Liu, P.V. 1966) |
| PGN4 | PAO1ΔtoxAΔplcH ΔphzMΔwapR | Non-mucoid, greenish colonies on PIA | This study |
| PGN5 | PAO1ΔtoxAΔplcH ΔphzMΔwapRΔaroA | Non-mucoid, white/tan colonies on PIA | This study |
| PGN5 + mucE | PAO1ΔtoxAΔplcH ΔphzMΔwapRΔaroA pUCP20-pGm-mucE | Mucoid, white/tan colonies on PIA | This study |
| PAO1$_{wpbL}$ | PAO1ΔwbpL | Produces no O-antigen | (Rochetta, et al. 1998) |
| *Escherichia coli* strains | | | |
| BL21 (DE3) | F − ompT hsdSB (rB− mB−) gal dcm (DE3) | FDA-approved for production of biopharmaceuticals; deficient in lon and ompT proteases | Lucigen, Middleton, WI, USA |
| DH5α | F− φ80dlacZΔM15 Δ(lacZYA-argF)U169 deoR recA1 endA1 hsdR17($r_K^-$ $m_K^+$) phoA supE44 λ− thi-1 gyrA96 relA1 | | Laboratory strain |
| TOP10 | F− mcrA Δ(mrr-hsd RMS-mcrBC) φ80lacZΔM15 ΔlacXPA recA1 araD139 Δ(ara-leu) 7697galU galK rpsL (Str$^R$) endA1 nupG λ− | Cloning and plasmid propagation | Invitrogen, CA, USA |
| SM10 (λpir) | thi recA thr leu tonA lacY supE RP4-2-Tc::Mu1::pir Km$^r$ | | Laboratory strain |

TABLE 2

Plasmids used.

| Plasmid | Relevant characteristics | Source |
|---|---|---|
| pEX100T-NotI | *Pseudomonas* suicide vector with NotI restriction site fused into SmaI of pEX100T sacB oriT Cb$^R$ | (Damron et al., 2009) |

TABLE 2-continued

Plasmids used.

| Plasmid | Relevant characteristics | Source |
|---|---|---|
| pRK2013 | Helper plasmid for conjugation, Km$^R$ | (Figurski et al., 1979) |
| pUCP20-pGm-mwcE | mucE over-expression under gentamicin promoter, Gm$^R$ | (Qiu et al., 2007) |
| pTNS2 | Helper plasmid; does not replicate in P. aeruginosa. Cb$^R$ | (Choi et al., 2006) |
| pUC18-mini-Tn7T-Gm-lux | Pseudomonas suicide vector that carries luxCDABE operon for insertion into attTn7 sites, Gm$^R$ | (Choi et al., 2006) |
| pFLP2 | Facilitates recombination between FRT sites, Cb$^R$ | (Choi et al., 2006) |

Figure 6:
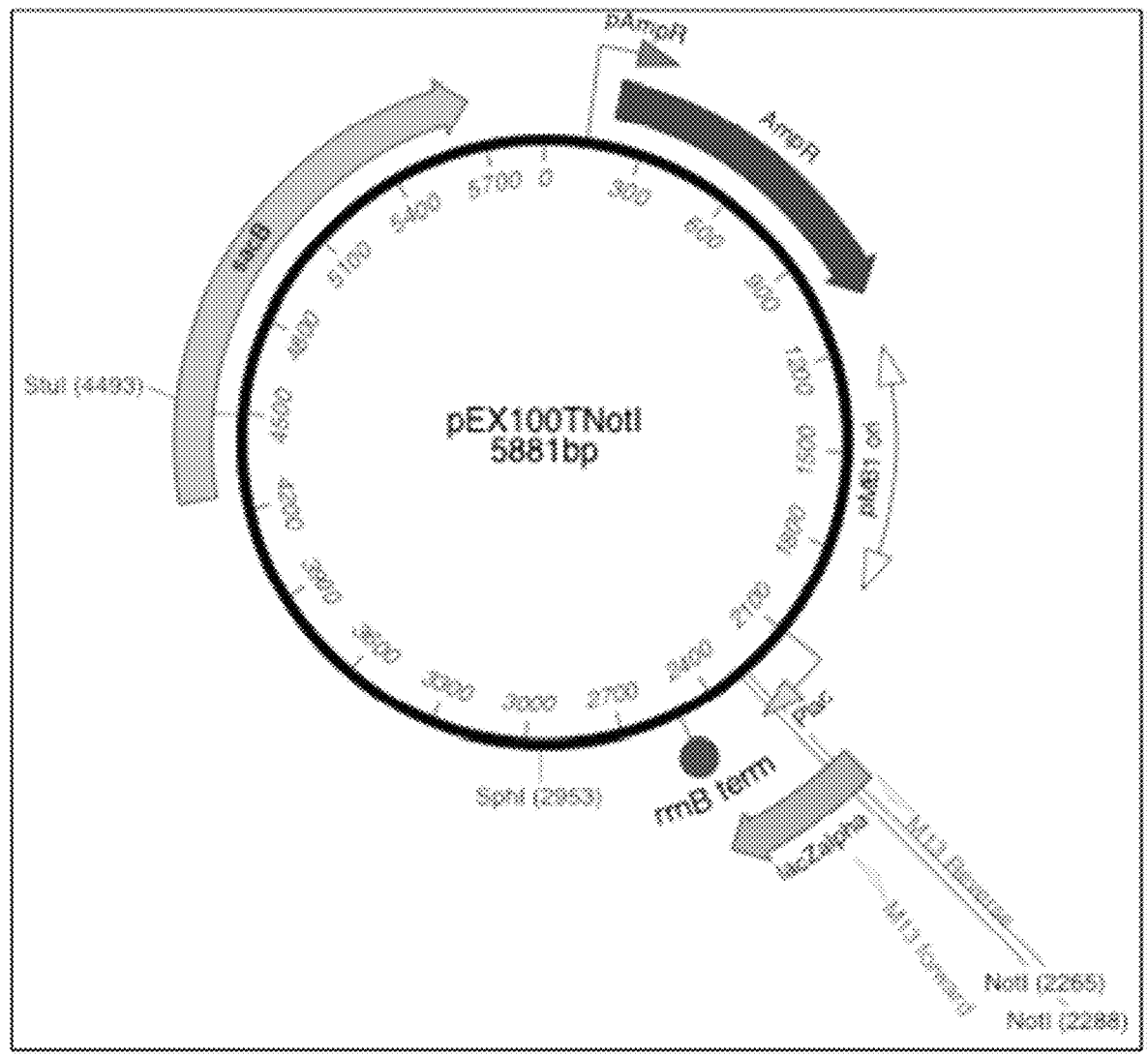
FIG. 6 is a diagram showing a *Pseudomonas* integration vector pEX100TNotI that was used to generate marker-free, in-frame deletion of pathogenicity genes in *P. aeruginosa* PAO1, where all deletion inserts were cloned into a NotI restriction site.

Gene deletions. Retrieval and analysis of P. aeruginosa gene sequences was performed using the Pseudomonas Genome Database website. For PGN5, five genes, toxA, plcH, phzM, wapR, and aroA were sequentially deleted from the chromosome of the wild-type P. aeruginosa strain PAO1. The pEX100T-NotI plasmid was used to mediate the in-frame marker-less deletion of each gene (FIG. 6). This plasmid carries the genes ampR, which confers resistance to carbenicillin, and sacB (B. subtilis), which provides sucrose sensitivity. Plasmid inserts used to delete toxA, plcH, phzM, and wapR were generated by PCR-amplification of 500-1000 bp of sequence directly upstream and 500-1000 bp of sequence directly downstream of each target gene (Table 3), followed by fusion of these DNA fragments via crossover PCR. The resultant PCR product was digested and ligated into pEX100T-NotI. For in-frame deletion of aroA, about 800 bp of upstream sequence adjacent to about 900 bp of downstream sequence of the target gene was synthesized, digested, and ligated into pEX100T-NotI by the company GenScript (Piscataway, NJ, USA). Each of the final plasmids was transformed into OneShot™ TOP10 Electrocomp E. coli (Invitrogen, Carlsbad, CA, USA).

For each deletion, the pEX100T-NotI plasmid carrying its specific insert was introduced into P. aeruginosa via triparental conjugation with the helper plasmid pRK2013. The target gene was deleted with a two-step allelic exchange procedure. Briefly, homologous recombination between one site on the plasmid and its target site on the chromosome integrated the plasmid into the P. aeruginosa chromosome (i.e., a single-crossover event). Single-crossovers were selected by plasmid-conferred resistance to carbenicillin and sensitivity to 10% (w/v) sucrose supplemented in PIA. Single-crossovers were grown overnight in LB broth to allow for homologous recombination between the second site on the plasmid with its target site on the chromosome (i.e., a double-crossover event), which removes the entire plasmid sequence along with the target gene sequence. Double-crossovers were selected by sensitivity to carbenicillin and resistance to sucrose, indicating that the plasmid sequence had been removed. Sucrose-resistant, carbenicillin-sensitive colonies were sequenced to verify the in-frame gene deletion.

To then generate PGN6, the algI and algJ genes were deleted from the PGN5 strain using two-step allelic exchange with the Pseudomonas gene deletion vector, pEX100TNot1, as described above. Subsequently to then generate a marker-free, attenuated strain of P. aeruginosa that could produce deacetylated alginate, identical to seaweed alginate, and devoid of G residues (polyM), algG was mutated in the PGN6 strain by introducing two mutations into the algG gene sequence (A971C, C972G) of the PGN6 strain using the two-step allelic exchange with Pseudomonas gene deletion vector, pEX100TNot1, as previously described.

TABLE 3

Generation of in-frame deletion mutant of P. aeruginosa for alginate production.

| Name | Genotype | PAO1 locus tag | Size (kb) | Missing gene product | Targeted virulence | Alginate |
|---|---|---|---|---|---|---|
| PGN1 | PAO1ΔtoxA | PA1148 | 1.9 | Exotoxin A | Major exotoxin | + |
| PGN2 | PGN1ΔplcH | PGN1 + PA0844 | 2.2 | Hemolytic phospholipase C | Membrane degrading enzyme | + |
| PGN3 | PGN2ΔphzM | PGN2 + PA4209 | 1.0 | Phenazine-specific methyltransferase | Pyocyanin (Pigment) | + |
| PGN4 | PGN3ΔwapR | PGN3 + PA5000 | 0.9 | Alpha-1,3-rhamnosyltransferase | Lipopolysaccharide O antigen | + |
| PGN5 | PGN4ΔaroA | PGN4 + PA3164 | 2.2 | 3-Phosphoshikimate 1-carboxyvinyltransferase | Aromatic amino acids (F, Y and W) | + |
| PGN6 | PGN5ΔalgIalgJ | PGN5 + PA3548, 3549 | 2.7 | Alginate O-acetyltransferases AlgI and AlgJ | Alginate acetylation | + |

Each of the in-frame deletions described above was further confirmed by PCR using the primers described in Tables 4 and 5 below.

TABLE 4

PCR Primers used to confirm in frame deletions.

| Deletion | Primers used | Expected PCR product size in PAO1 (bp) | Expected PCR product size in PGN5/6 (bp) |
|---|---|---|---|
| toxA | toxA forward: AATTCATATTCGATTGGGCTGGCATCAGG (SEQ ID NO: 1)<br>toxA reverse: GTTCGCACATTCACCACTCTGCAATCC (SEQ ID NO: 2) | 2195 | 284 |
| plcH | plcH forward: CAGTTGCTCTTCCTCGCCAGG (SEQ ID NO: 3)<br>plcH reverse: CATGAACAAGTGACCTTTCATTCAGCCGACAAGG (SEQ ID NO: 4) | 2941 | 769 |
| phzM | phzM forward: AACTGGCGCAGGCGGAGACC (SEQ ID NO: 5)<br>phzM reverse: GGATTGCTAAGCTGATGCTTCCTGCAATGC (SEQ ID NO: 6) | 1438 | 448 |
| wapR | wapR forward: AGCCGTTCTGCTAGCCTCGACC (SEQ ID NO: 7)<br>wapR reverse: TGAGAGTAGCAGCCGAAAAGAGCTGG (SEQ ID NO: 8) | 1259 | 374 |
| aroA | aroA forward: GCGAACGCCAACAGCCGATAAAGC (SEQ ID NO: 9)<br>aroA reverse: ATCTGGCTCGCGATGCCGGTCC (SEQ ID NO: 10) | 2548 | 334 |
| algI-algJ | algIJ forward: CGACCTGAATGGTTGACGCTC (SEQ ID NO: 11)<br>algIJ reverse: AAGCGATGCGTCTGTCTAGGGAT (SEQ ID NO: 12) | 3695 | 942 |

TABLE 5

Additional PCR Primers used to confirm in frame deletions/insertions.

| Gene | Primers used | Expected PCR product size in PAO1 with HhaI digestion (bp) | Expected PCR product size in PGN6-polyM with HhaI digestion (bp) |
|---|---|---|---|
| algG | algG forward: GCCCCAAGGGCTGGGTGATCG (SEQ ID NO: 13)<br>algG reverse: GCGCACGCGGATGCCGTGG (SEQ ID NO: 14) | 421 | 127 + 294 |

Gene sequencing. Sanger sequencing to confirm in-frame deletions was performed by the West Virginia University (WVU) Genomics Core Facility (Morgantown, WV, USA). Whole genome resequencing on these strains was performed by CD Genomics (Shirley, NY, USA). Genomic assembly of the data utilized the SPAdes microbial isolate assembler followed by transfer annotation using PROKKA. Homology based taxonomy assignment utilized PanGIA, along with in-house derived confidence level settings based on positive control DNA mixtures. Reference based analysis employed Bowtie2 compared to the parental strain genome (GenBank accession number AE004091.2) with variant calling. Bowtie2 settings include a 1000 nt window and a 200 nt step size. Whole genome sequences have been deposited for PGN4 (GenBank accession number CP032540) and PGN5 (GenBank accession number CP032541), which are each incorporated herein by reference in their entirety.

Western blot for Exotoxin A. A Western blot was used to verify the deletion of toxA in PGN5 by absence of the Exotoxin A product. Cells from 24-h broth cultures of P. aeruginosa strains PAO1, Exotoxin A-positive PA103, and PGN5 were removed by centrifugation. Supernatant was filter-sterilized with a 0.2 μm syringe filter and concentrated with an Amicon Ultra-15 Centrifugal Filter Unit with a 10-kDa cutoff (Sigma, St. Louis, MO, USA) according to the manufacturer's instructions. Total protein concentration of the supernatant was quantified with the bicinchoninic acid assay (BCA) using a bovine serum albumin (BSA) standard (Pierce, Rockford, IL, USA). Samples with equal total protein concentrations (0.05 μg/μL) were run on the ProteinSimple Wes automated Western blot system using the 12-230 kDa separation module and the 8×25 capillary cartridge (San Jose, CA, USA). Exotoxin A was detected with a polyclonal rabbit anti-Exotoxin A antibody (Sigma, St. Louis, MO, USA) diluted 1:200, and the ProteinSimple anti-rabbit detection module (San Jose, CA, USA).

Analysis of hemolytic activity. To verify deletion of plcH, hemolytic activity of E. coli strain BL21 and P. aeruginosa strains PAO1, VE2, and PGN5 was assessed by culturing bacterial strains for 48 h on blood agar (trypticase soy agar with 5% sheep blood; Remel, Lenexa, KS, USA). Before inoculation, plates were treated with a 1 mg/mL solution of aromatic amino acids and dried. Plates were imaged for the presence or absence of clear plaques indicating hemolysis surrounding bacterial growth.

Extraction and quantification of pyocyanin. To verify deletion of phzM in PGN5, a two-step extraction procedure with chloroform and HCl was used to recover and quantify the secreted pyocyanin pigment. Briefly, cells from 24-h broth cultures of *P. aeruginosa* strains PAO1 and PGN5 were removed by centrifugation at and the supernatant was filter-sterilized with a 0.2 µm syringe filter. Pyocyanin was extracted from 7.5 mL samples with 4.5 mL of chloroform. Pyocyanin was reextracted from 3 mL of the chloroform layer with 1.5 mL of 0.2 M HCl to give a pink color. The absorption at 520 nm ($A_{520}$) of the aqueous HCl layer was measured with a SmartSpec™ 3000 spectrophotometer (BioRad, Hercules, CA, USA) and pyocyanin concentration was calculated as follows:

$$A_{520} \times 17.072 \times 1.5 = \text{pyocyanin concentration (in µL/mL)}.$$

LPS extraction, silver staining, and Western blot for O-antigen. To verify deletion of wapR, lipopolysaccharides (LPS) were analyzed for the presence of O-antigen. LPS were extracted using the Hitchcock and Brown method, resolved by electrophoresis on 12% SDS-PAGE, and stained for visualization using an ultrafast silver staining method. For Western immunoblotting, LPS was transferred onto BioTraceNT nitrocellulose membranes (Pall) and detected with a 1:1 mixture of monoclonal antibodies MF15-4 (OSA specific) and 5c-7-4 (inner core specific) overnight at room temperature, followed by incubation with an alkaline phosphatase-conjugated goat anti-mouse $Fab_2$ secondary antibody (Jackson ImmunoResearch, West Grove, PA, USA). The blots were developed using nitroblue tetrazolium (NBT) and 5-bromo-4-chloro-3-indolylphosphate (BCIP) as described previously.

ELISA for AroA. An enzyme-linked immunosorbent assay (ELISA) was used to verify deletion of aroA by determining the absence of the 3-phosphoshikimate 1-carboxyvinyltransferase product. A 96-well untreated plate was coated with equal amounts of carbonate buffer and of broth culture of the *P. aeruginosa* strains PAO1 and PGN5. The plate was then incubated for 2 h at 37° C. and blocked in skim milk overnight. A polyclonal rabbit anti-AroA primary antibody (LifeSpan BioSciences, Inc., Seattle, WA, USA) and a polyclonal goat anti-rabbit IgG secondary antibody (Sigma, St. Louis, MO, USA) were used to detect 3-phosphoshikimate 1-carboxyvinyltransferase. Samples were incubated in 1-Step™ Ultra TMB ELISA Substrate Solution (Thermo Scientific, Rockford, IL, USA), followed by addition of acid stop solution (R&D Systems, Minneapolis, MN, USA). The absorbance was immediately measured at 450 nm ($A_{450}$) on a Molecular Devices Spectramax® i3x microplate reader (Molecular Devices, Sunnyvale, CA, USA). Absorbance reported was the relative absorbance detected between PAO1 and PGN5.

Carbazole assay. The carbazole assay is a standard uronic acid detection method that was used to quantify the amount of alginate produced in culture. The *P. aeruginosa* strains VE2 and PGN5+mucE were grown on PIA for 48 h at 37° C. Alginate and cells were collected with 0.85% NaCl. Cell suspensions were incubated in sulfuric acid/borate solution and carbazole at 55° C. As carbazole reacts with uronic acid, the solution turns a pink to purple color. Absorbance at 530 nm ($A_{530}$) was measured on a SmartSpec™ 3000 spectrophotometer. The concentration of alginate (µg/AU [absorbance unit]) was calculated using a standard curve generated with purified mannuronic alginic acid (Sigma, St. Louis, MO, USA).

Compositional analysis of alginate via HPLC. Determination of the M:G sugar ratios in bacterial alginate was performed by HPLC analysis following pre-column derivatization of hydrolyzed alginate with 1-phenyl-3-methyl-5-pyrazolone (PMP). Alginic acid from broth cultures of *P. aeruginosa* strains VE2 and PGN5+mucE was precipitated with 3 volumes of ethanol, vacuum filtered through a Twill Dutch weave wire cloth (5 µm; Dorstener Wire Tech, Spring, TX, USA), and dried in a vacuum oven. Five mg of dried alginic acid was suspended in 1 ml of 3 M trifluoroacetic acid (TFA) and hydrolyzed in a sealed vial at 110° C. After 2 h, the samples were cooled to room temperature, combined with dry methanol (1 mL), and dried by vacuum centrifugation. Water (0.3 mL), 0.3 M NaOH (0.15 mL), and 0.5 M PMP (0.15 mL) were then added to the hydrolyzed alginate and the pH was adjusted to 9 to 9.5 with 0.3 M NaOH. The samples were sealed and incubated at 70° C. for 1.5 h with shaking at 1,200 rpm. On completion of the derivatization reaction, the excess PMP reagent was removed by repeated extraction with chloroform (1 mL). The extraction procedure was performed until the chloroform layer (bottom) was free from color following vortex and centrifugation at 13,000 rpm. The aqueous layer (top) containing the derivatized M/G monomers was then passed through a 0.45 µM PTFE syringe filter and analyzed by HPLC. Spectrophotometric detection of the derivatized monomers was performed using an Agilent Infinity II HPLC system equipped with a 1260 quaternary pump (G7111B), vial sampler (G7129A), multicolumn thermostat (G7116A), diode array detector (G7115A) and Openlab CDS ChemStation Edition (v. C.01.08 [210]) software. Chromatographic separation was performed using an Agilent Eclipse Plus C18 column (4.5×150, 3.5 µM) and a mobile phase consisting of 0.1 M phosphate buffer (pH 6.7) with acetonitrile at a ratio of 83:17 (v/v %). The column temperature was maintained at 25° C. and elution of the derivatized M/G monomer was detected at 245 nm. As a control, commercially available alginic acid from brown algae (A7003; Sigma, St. Louis, MO, USA) was prepared and run along with *P. aeruginosa* alginate samples.

Physical property testing of alginate. To test the physical properties of bacterial alginates, sodium alginate gels were prepared from dried alginic acid (prepared as described above). Briefly, alginic acid was dissolved in NaOH pH 8.5-9 to form sodium alginate, which was then precipitated with ethanol, filtered, and dried in a vacuum oven. Sodium alginate gels (2% w/v) were prepared by dissolving sodium alginate in distilled water. Viscosity and yield stress were measured on a HAAKE MARS I Rheometer (Thermo Scientific, Karlsruhe, Germany) using preset parameters. Analysis and calculations were performed with RheoWin Software (version 4.82, Thermo Scientific, Karlsruhe, Germany).

Bacterial pathogenicity in mice. *P. aeruginosa* strains PGN5 and VE2, and *E. coli* strain BL21 were grown in LB broth to generate frozen stocks for injection into C57BL/6 mice. Cell cultures were concentrated to $2.5 \times 10^9$ cells per mL, flash frozen in liquid nitrogen, and stored at −80° C. The cultures used were strain-verified by PCR and phenotype, and cell concentrations were verified by viable plate counts before freezing and before mouse injection. A total of eighty 10- to 12-week-old mice was divided into 4 groups of 10 males and 10 females. Each group received 200 µL intraperitoneal injections of one of the following: PBS, $5 \times 10^8$ cells of the *P. aeruginosa* strains VE2 or PGN5+mucE, or 5×10$^8$ cells of the *E. coli* strain BL21. After injection, mice were monitored for mortality every 3 h for 72 h, and then every 12 h for 7 days.

Localization of bioluminescent bacteria in mice. PAO1 and PGN5 were marked with bioluminescence using the method and plasmids developed in the Schweizer lab. The pUC18 mini-Tn7T-Gm-lux plasmid was used, which allows for insertion of the luxCDABE operon, along with an FRT-flanked gentamicin resistance cassette into a neutral site downstream of the glmS gene. Briefly, electrocompetent PAO1 and PGN5 cells were prepared with sucrose and electroporated with the pUC18 mini-Tn7T-Gm-lux and pTNS2 plasmids. Pure stocks were generated from resultant gentamicin-resistant and bioluminescent colonies. The pFLP2 plasmid was used to remove the gentamicin-resistance cassette. Final stocks used for mouse injection were bioluminescent, plasmid cured, and gentamicin and carbenicillin sensitive. For mouse injection, stocks were prepared and injected as described above. Mice were imaged on an IVIS Lumina XRMS (PerkinElmer, Waltham, MA, USA) every 6 h for 18 h and monitored for 4 weeks. By 18 h post-injection, bioluminescence was only detected at the injection site of all mice.

Statistical analyses. GraphPad Prism 7.02 for Windows (GraphPad Software, La Jolla, CA, USA) was used to generate graphs and perform statistical analyses (two-tailed Student's t-test).

Example 1—Deletion of Five Key Pathogenicity Genes in *P. aeruginosa*

Figure 7:
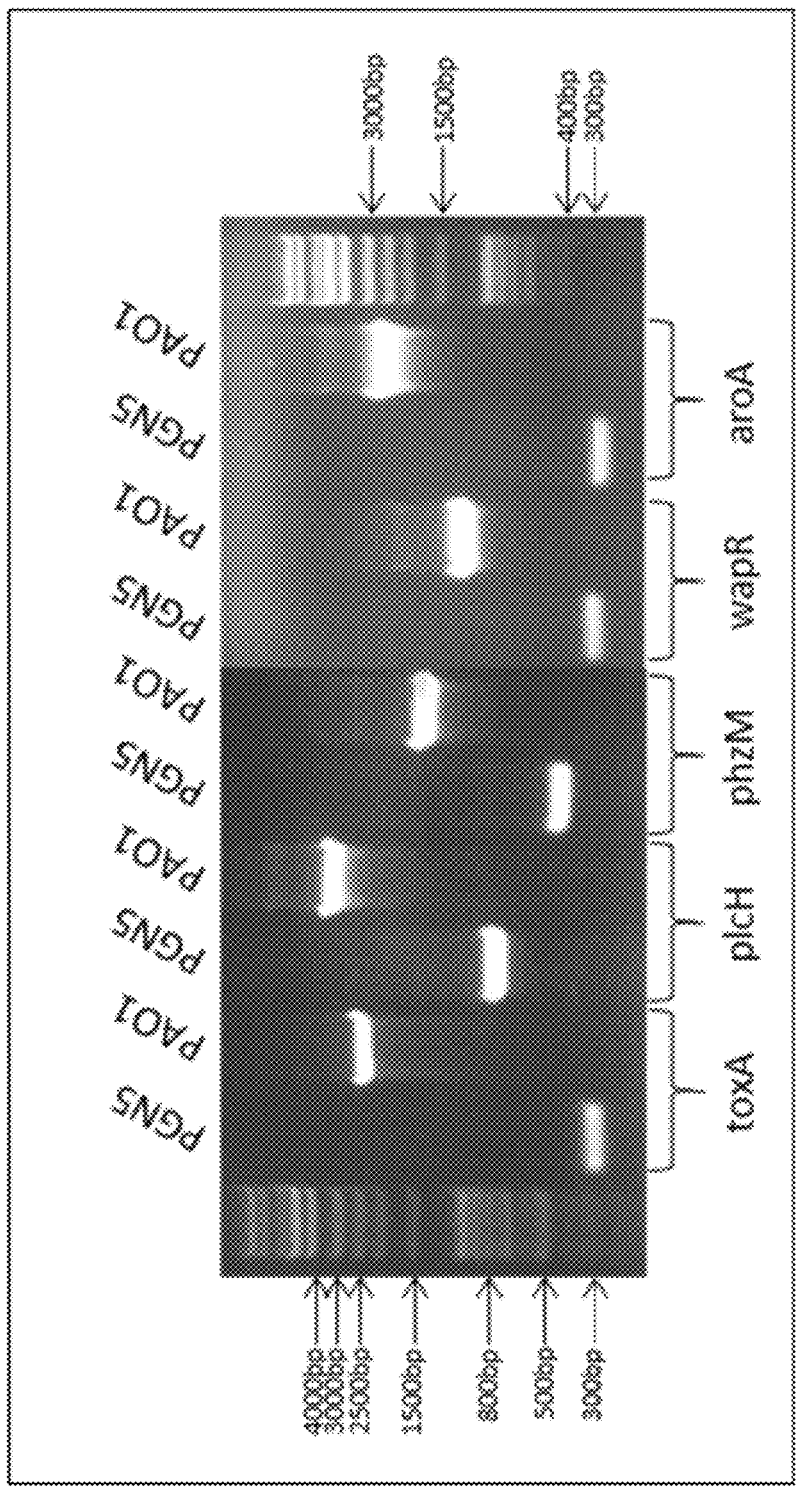
FIG. 7 is an image of a gel showing that PGN5 contains in-frame deletions of the genes required for the production of exotoxin A (toxA), phospholipase C (plcH), pyocyanin (phzM), O-antigen assembly (wapR), and aromatic amino acid biosynthetic gene (aroA). Using the suicide vector pEX100TNotI and two-step allelic exchange, toxA, plcH, phzM, wapR and aroA were sequentially deleted from PAO1.
Figure 8:
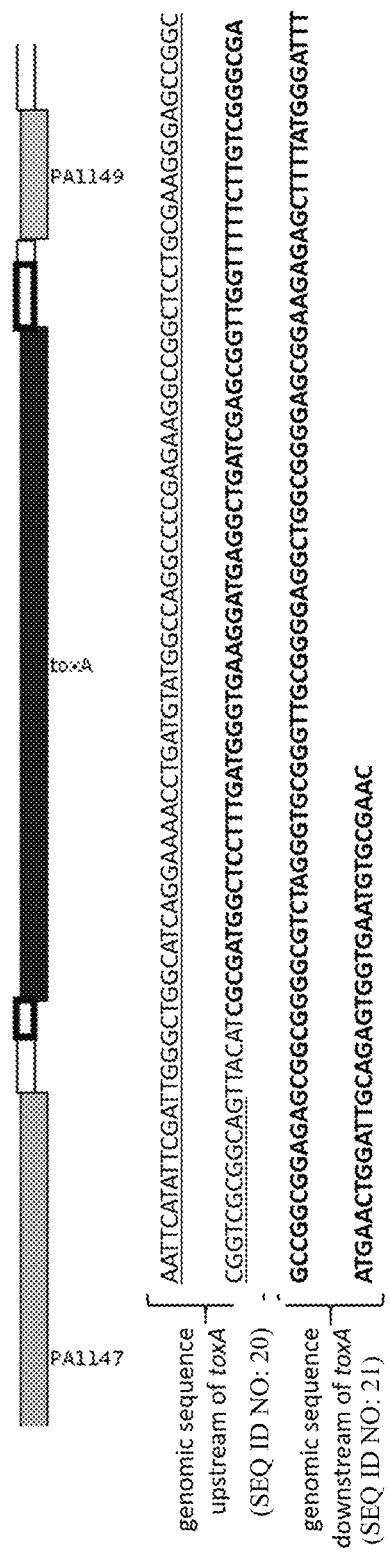
FIG. 8 is a diagram and sequence showing that the toxA gene deletion was confirmed by sequencing in PGN5. Genomic regions upstream and downstream of toxA were sequenced, but no toxA sequence was detected. Similar results were obtained through sequencing plcH, phzM, wapR, and aroA.
Figure 9:
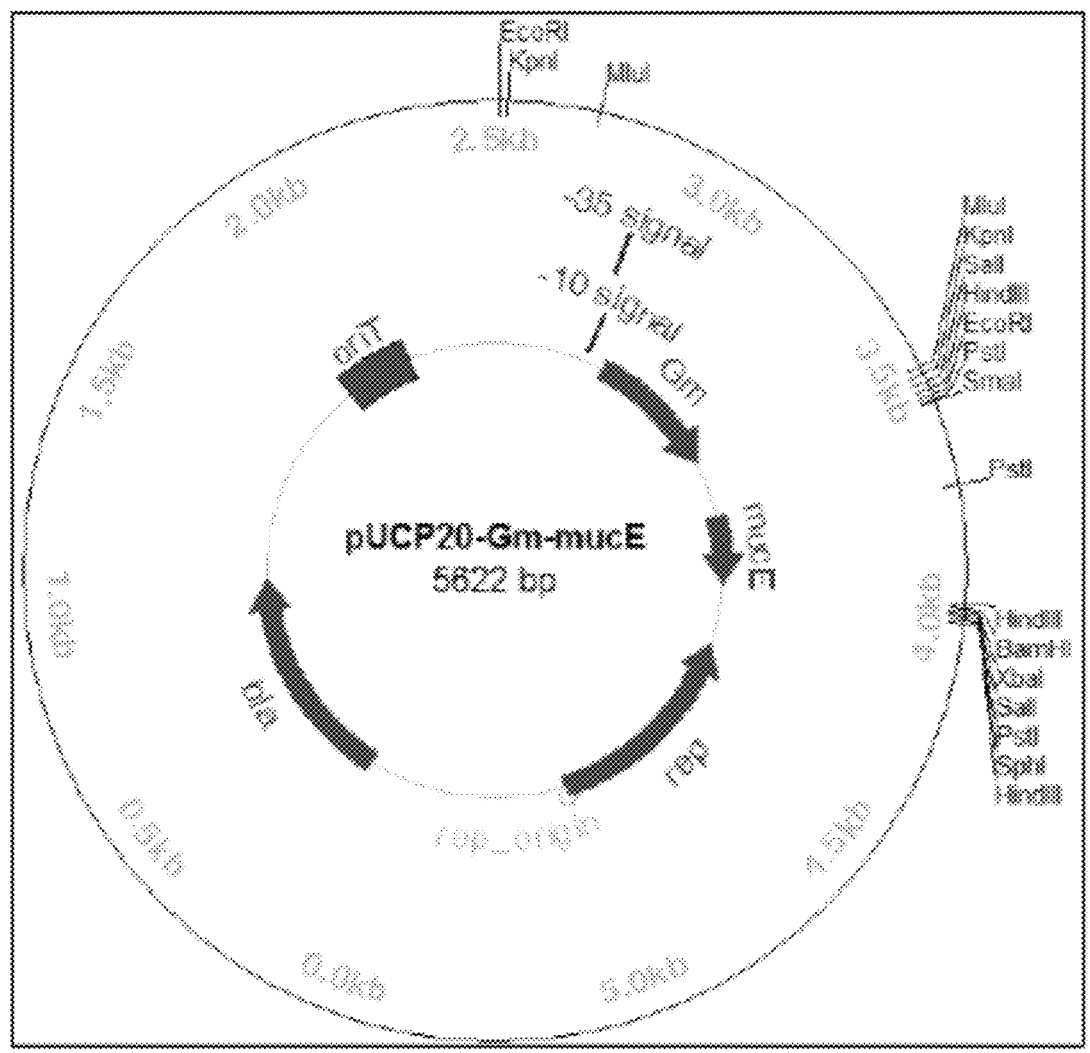
FIG. 9 is a diagram showing a plasmid that contains mucE encoding a small periplasmic protein that activates the alginate biosynthetic pathway in *P. aeruginosa*.
Figure 10:
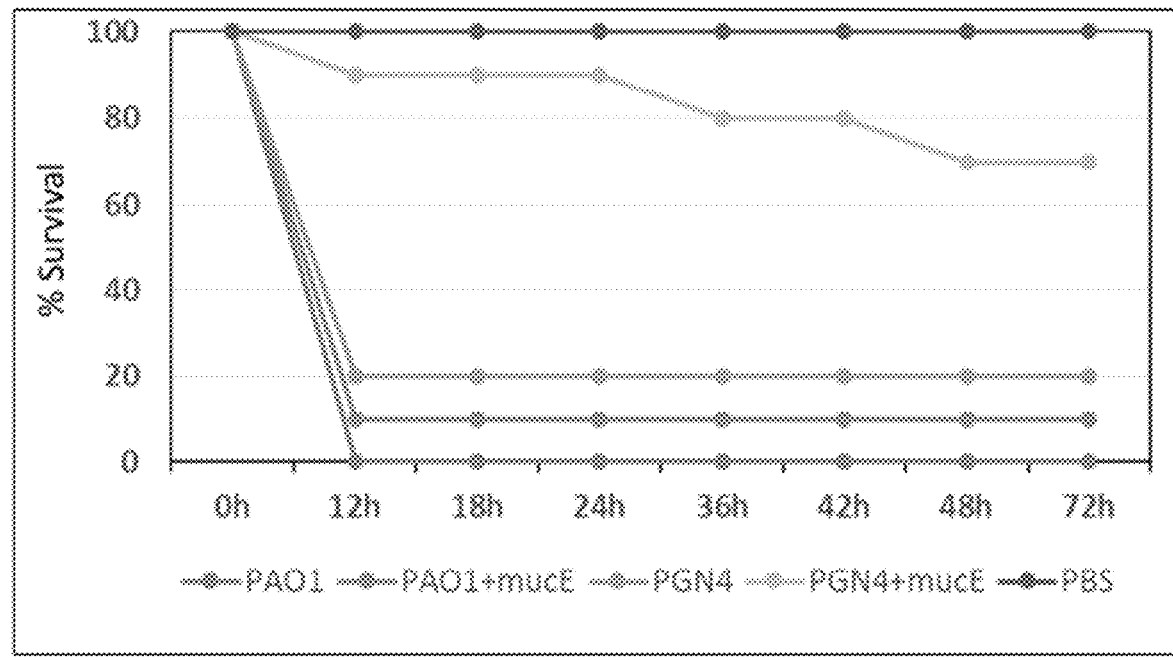
FIG. 10 is a graph showing that induction in the PGN4 strain reduces pathogenicity in a murine model. The percent survival of male C57BL/6 mice is plotted over time (n=10 mice per group) with each mouse receiving a comparable dose of $1\times10^8$ CFU via intraperitoneal injection.
Figure 11:
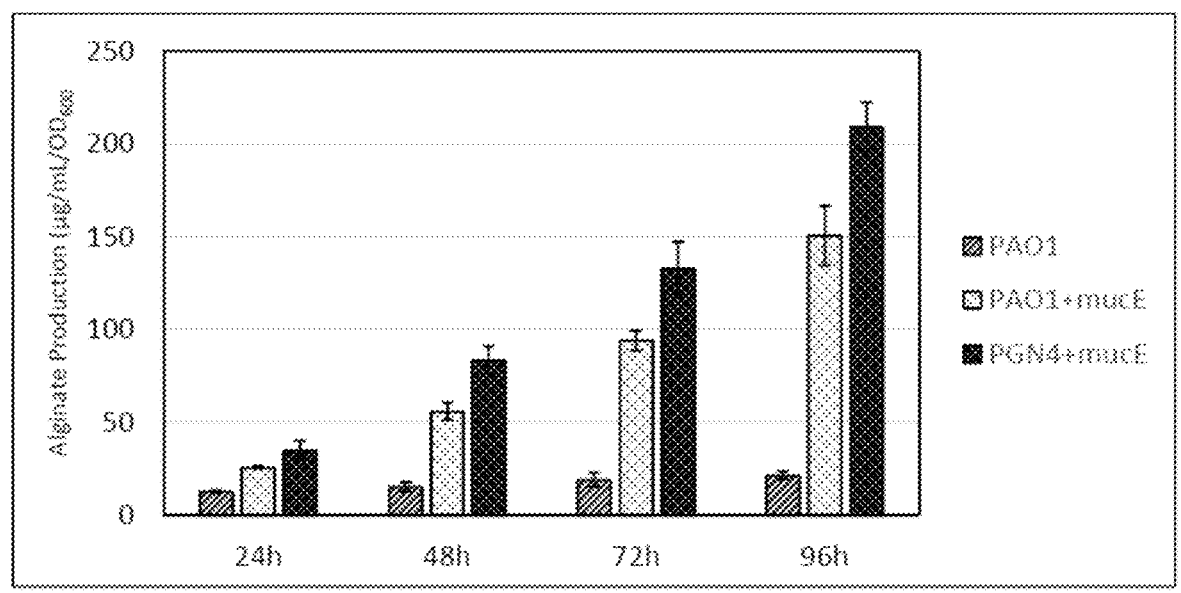
FIG. 11 is a graph showing that PGN4 is capable of producing alginate. PAO1, PAO1 pUCP20T-PGm-mucE and PGN4 pUCP20T-PGm-mucE were cultured in 250 mL of *Pseudomonas* Isolation Broth (PM) with 2% glycerol. Samples were collected at 24 h, 48 h, 72 h and 96 h and analyzed using the standard carbazole assay for the presence of alginate. Presented are the mean and standard error of three experiments.

To generate an attenuated strain of *P. aeruginosa* for production of alginate, the following virulence factor genes were sequentially deleted from the chromosome of the wild-type strain PAO1: toxA, plcH, phzM, wapR, and aroA. toxA encodes the secreted toxin Exotoxin A, which inhibits protein synthesis in the host by deactivating elongation factor 2 (EF-2). plcH encodes the secreted toxin hemolytic phospholipase C, which acts as a surfactant and damages host cell membranes. phzM encodes phenazine-specific methyltransferase, an enzyme required for the production of the redox active, pro-inflammatory, blue-green secreted pigment, pyocyanin. wapR encodes a rhamnosyltransferase involved in synthesizing O-antigen, a component of lipopolysaccharide (LPS) of the outer membrane of the organism. aroA encodes 3-phosphoshikimate 1-carboxyvinyltransferase, which is required intracellularly for aromatic amino acid synthesis. Deletion of aroA from the *P. aeruginosa* genome has previously been shown to attenuate the pathogen. Each gene was successfully deleted using a homologous recombination strategy with the pEX100T-Not1 plasmid. The in-frame, marker-less deletion of these five gene sequences was verified by Sanger sequencing and by whole genome re-sequencing (FIG. 1 and FIG. 8). This engineered strain was designated as PGN5. The whole genome sequence of PGN5 has been deposited to NCBI Genbank with an accession number of CP032541. All five in-frame gene deletions were detected and validated to be the deletion as designed using PCR (FIG. 7).

Figure 2A:
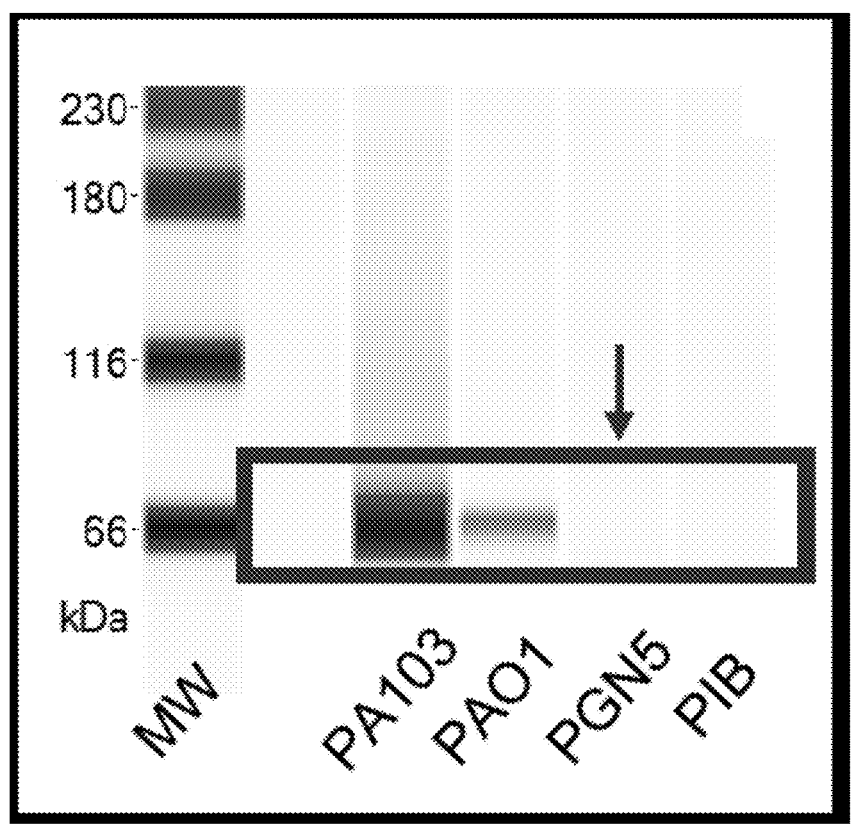
FIGS. 2A-2E include images and graphs showing confirmation of loss of deleted gene products in *P. aeruginosa* strain PGN5.
Figure 2B:
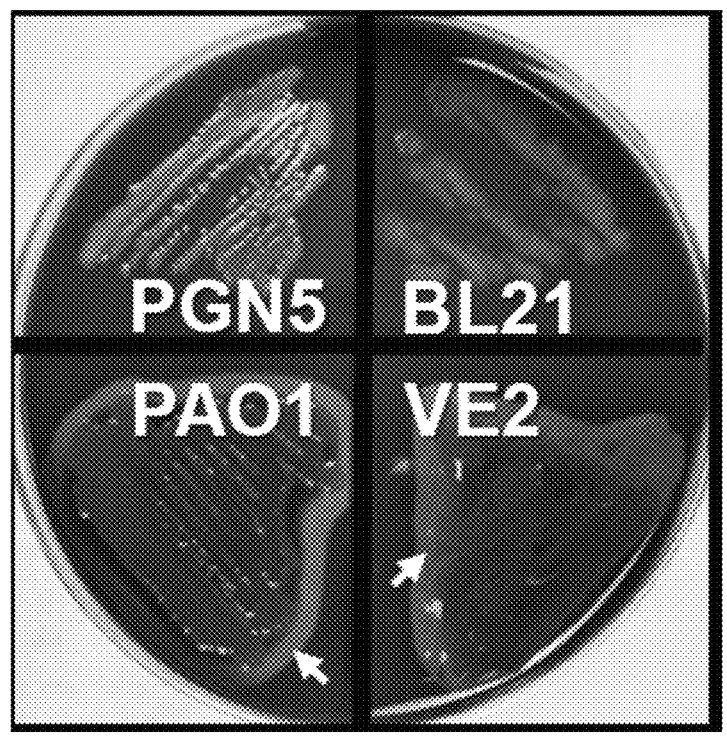
Figure 2C:
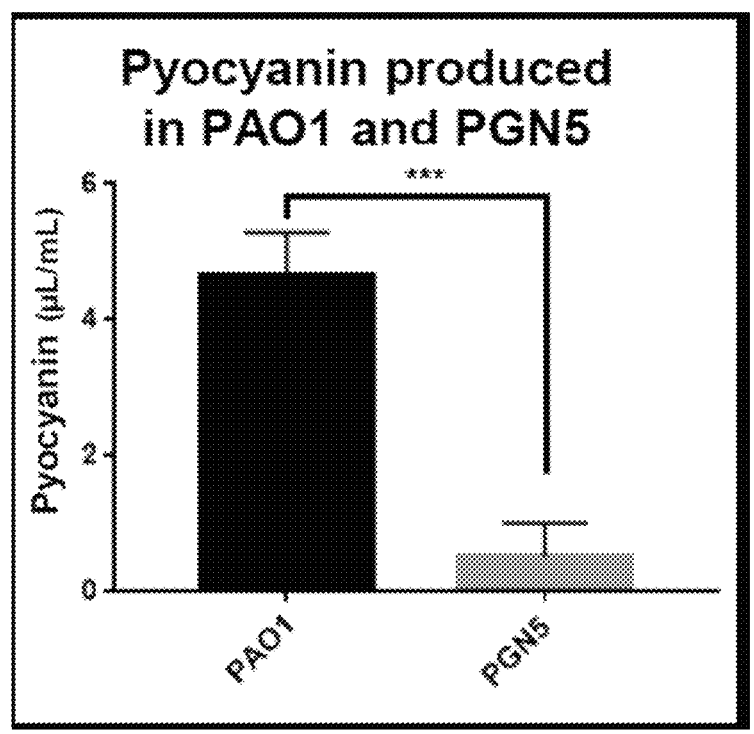
Figure 2D:
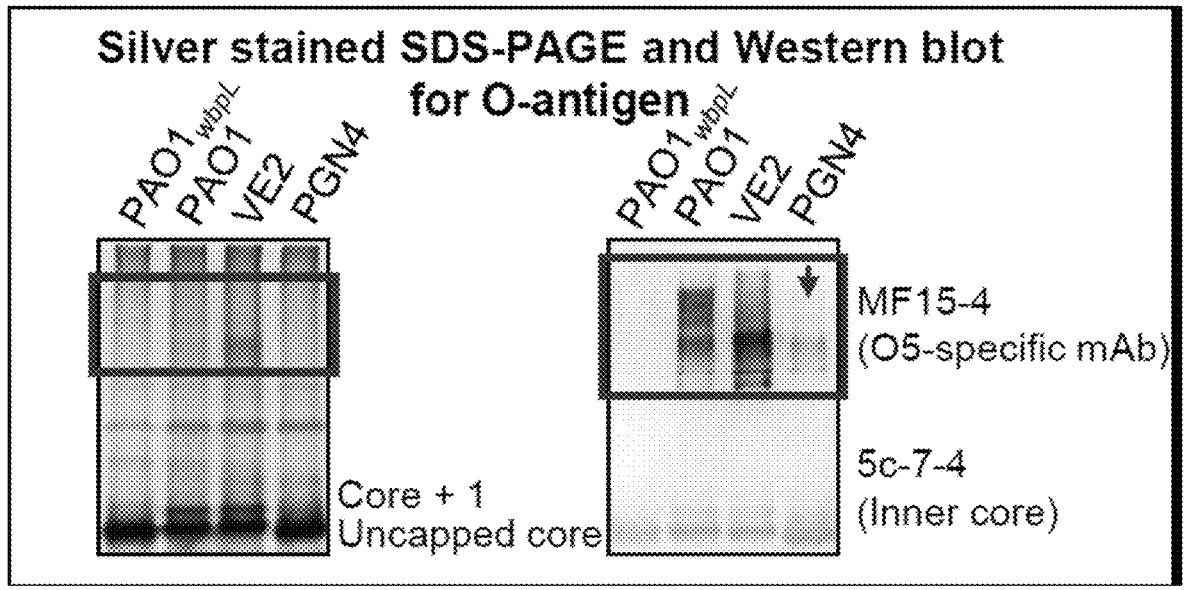
Figure 2E:
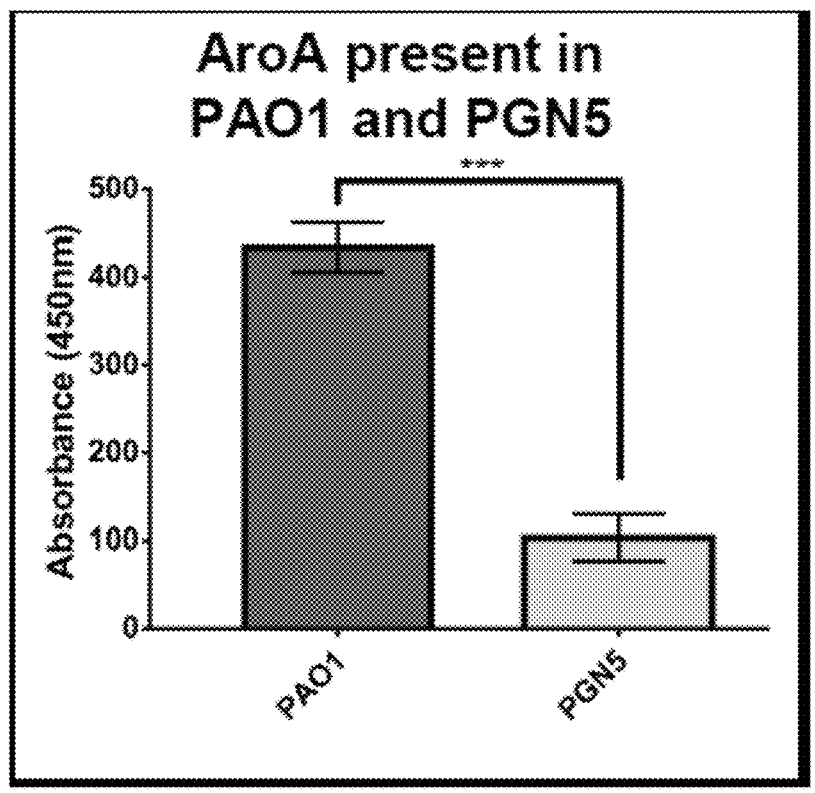
Figure 3A:
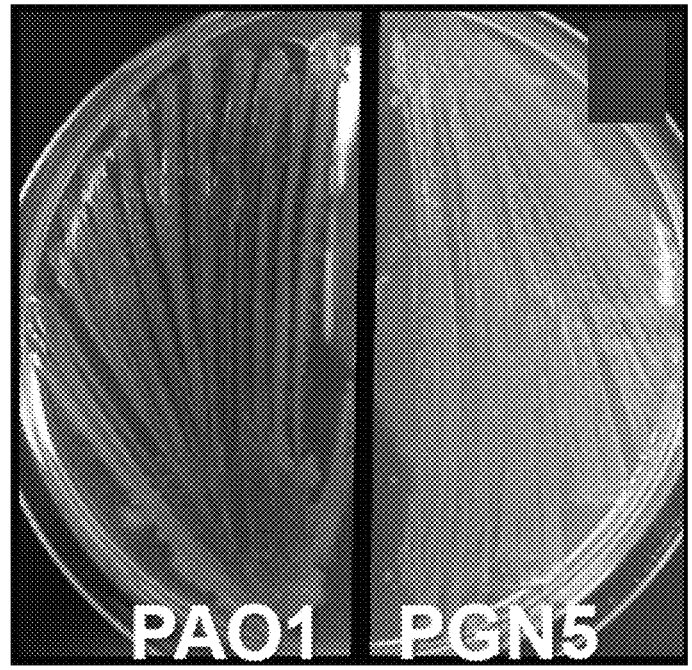
FIGS. 3A-3F include images and graphs showing phenotype and alginate characterization of *P. aeruginosa* strain PGN5.
Figure 3B:
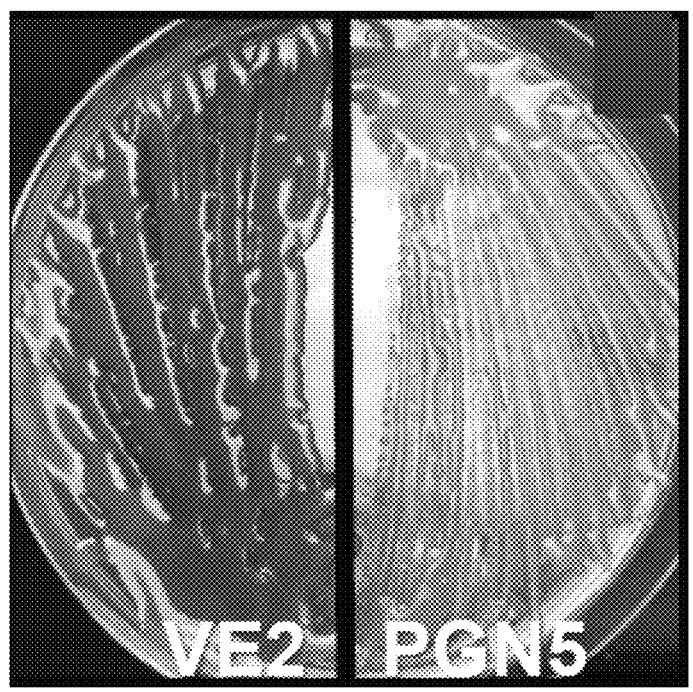

To verify gene deletion and attenuation of the PGN5 strain, the presence of the products of the deleted genes was measured and was either undetectable, or significantly reduced in the PGN5 strain. To test for the toxA gene deletion in PGN5, a Western blot analysis was performed for the presence of Exotoxin A in the culture medium. Exotoxin A secretion was detected in wild-type PAO1 control, but not in the PGN5 strain (FIG. 2A). To confirm the loss of plcH, hemolysis was assessed on blood agar. The hemolytic assay was carried out by streaking PAO1, PGN5, *P. aeruginosa* mucoid strain VE2, and a negative control, *Escherichia coli* strain BL21 on blood agar plates. A clear zone was observed surrounding PAO1 and VE2 cell growth, indicating complete (β-) hemolysis (FIG. 2B). In contrast, the blood agar remained red and opaque surrounding PGN5 and BL21 growth, indicating negligible or no hemolytic activity in these strains (FIG. 2B). To assess for deletion of phzM, the amount of pyocyanin secreted by PAO1 and PGN5 was extracted and measured. The amount of pyocyanin detected was significantly reduced in PGN5 (FIG. 2C). In fact, the difference in pigment production between PAO1 and PGN5 was immediately apparent on agar plates (FIGS. 3A-3B). To test for wapR gene deletion, an LPS extraction was performed, followed by silver-stained SDS-PAGE and Western blot on the following strains: PAO1, PGN4 (PGN5 without aroA deletion), VE2, and PAO1$_{wbpL}$, which serves as a negative control due to a deletion in the O-antigen ligase gene, and thus produces no O-antigen. The presence of O-antigen was detected in PGN4, but the level of LPS banding was significantly reduced compared to the LPS banding profile observed in PAO1 and VE2 (FIG. 2D). Lastly, to test for aroA deletion, ELISA was performed to detect the presence of 3-phoshoshikimate 1-carboxyvinyl-transferase in cell lysates prepared from PAO1 and PGN5. The ELISA results showed that the amount of 3-phosphoshikimate 1-carboxyvinyltransferase was significantly reduced in PGN5, compared to that in PAO1 (FIG. 2E). Additionally, the deletion of aroA resulted in slower growth in the PGN5 strain, a growth defect that was restored with the addition of 1 mg/mL of aromatic amino acids (W, Y, F) to the culture medium (data not shown).

Example 2—*P. aeruginosa* Strain PGN5 Produces a High Amount of Alginate

Figure 3C:
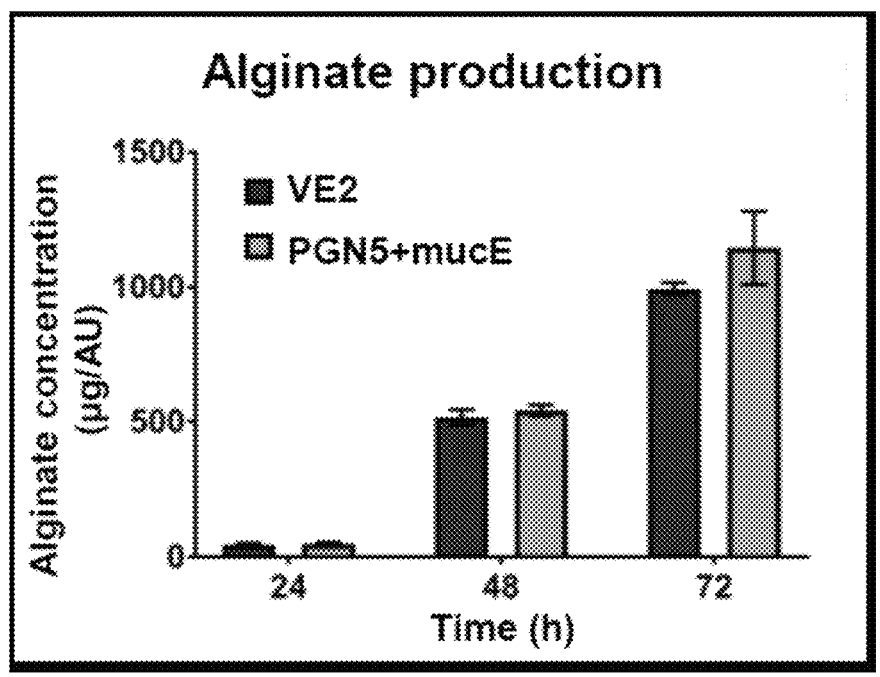

PAO1, the parent strain of PGN5, is a wild-type *P. aeruginosa* strain that produces relatively small amounts of alginate and exhibits a non-mucoid phenotype; thus, PGN5 is also non-mucoid when cultured (FIG. 3A). In PAO1, the alginate biosynthetic operon, which contains genes required for alginate production, is negatively regulated. Activation of this operon leads to alginate production and a mucoid phenotype. For example, over-expression of mucE, an activator of the alginate biosynthetic pathway, induces a strong mucoid phenotype in the PAO1 strain (e.g., *P. aeruginosa* strain VE2; FIG. 3B). The plasmid pUCP20-pGm-mucE, which constitutively over-expresses MucE, was used to test whether the genetically-modified PGN5 strain could produce alginate. Indeed, the presence of this plasmid in PGN5 (PGN5+mucE) induced a mucoid phenotype (FIG. 3B). To measure the amount of alginate produced by PGN5+mucE on a cellular level, a standard carbazole assay was performed, which showed that the PGN5+mucE and VE2 (i.e., PAO1+mucE) strains produce comparable amounts of alginate (FIG. 3C; 80-120 g/L wet weight).

Figure 3D:
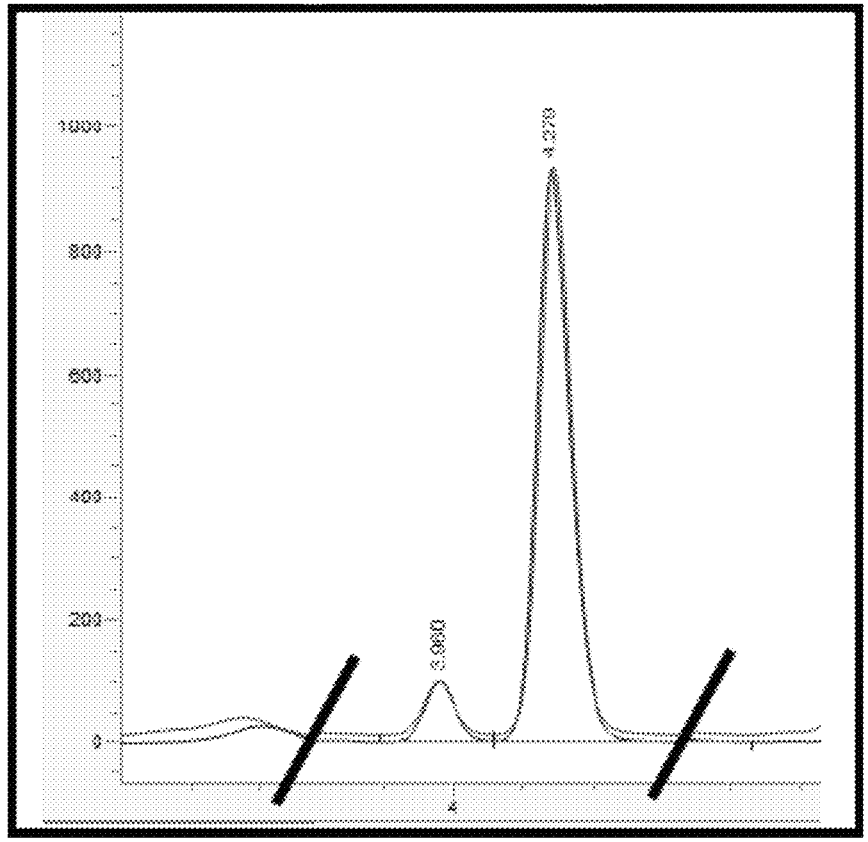
Figure 3E:
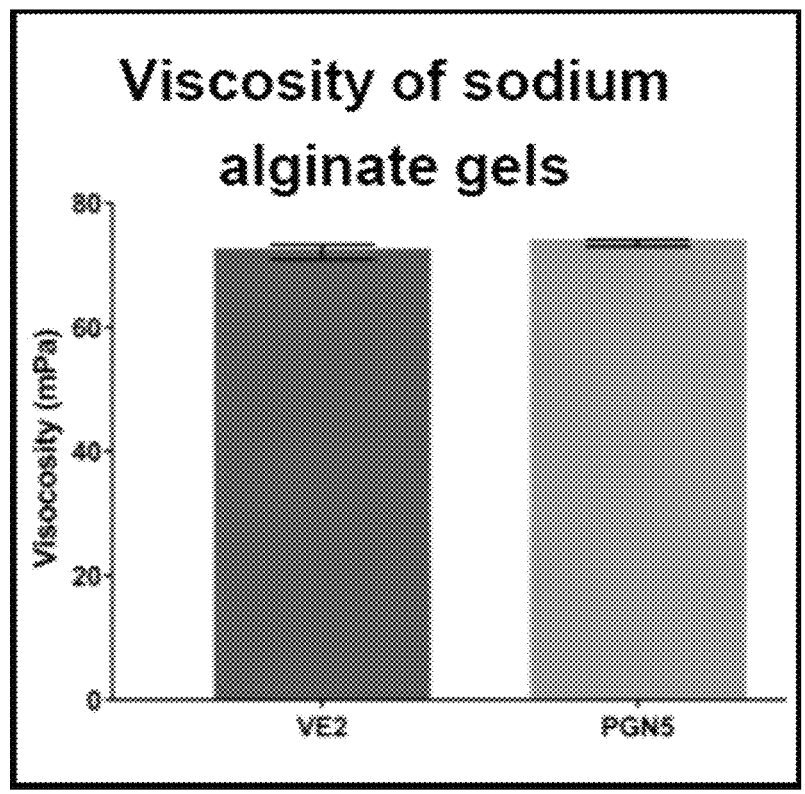
Figure 3F:
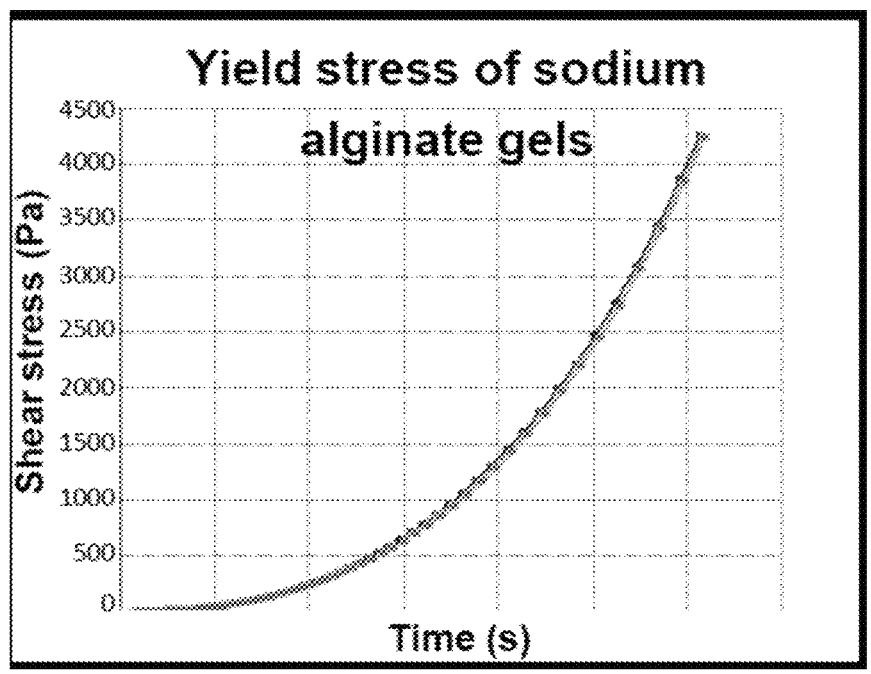

To examine whether the alginate produced by PGN5+mucE was similar in composition to alginate produced by VE2, HPLC was performed to compare the M and G content of alginate produced by each strain. The chromatograms obtained from alginate prepared from VE2 and PGN5+mucE were identical (FIG. 3D), and the M:G ratios were comparable to a commercial alginate control (data not shown). To confirm that the physical properties of VE2 and PGN5+mucE alginates were also similar, alginate gels were prepared from alginate produced by each strain and the viscosity and yield stress was measured. The viscosities of VE2 and PGN5+mucE alginate gels were comparable at 73.58 and 72.12 mPa, respectively (FIG. 3E). Similarly, the yield stress of VE2 and PGN5+mucE alginate gels were comparable at 47.34 and 47.16 Pa, respectively (FIG. 3G).

Example 3—*P. aeruginosa* Strain PGN5 did not Cause Mortality in Mice

Figure 4A:
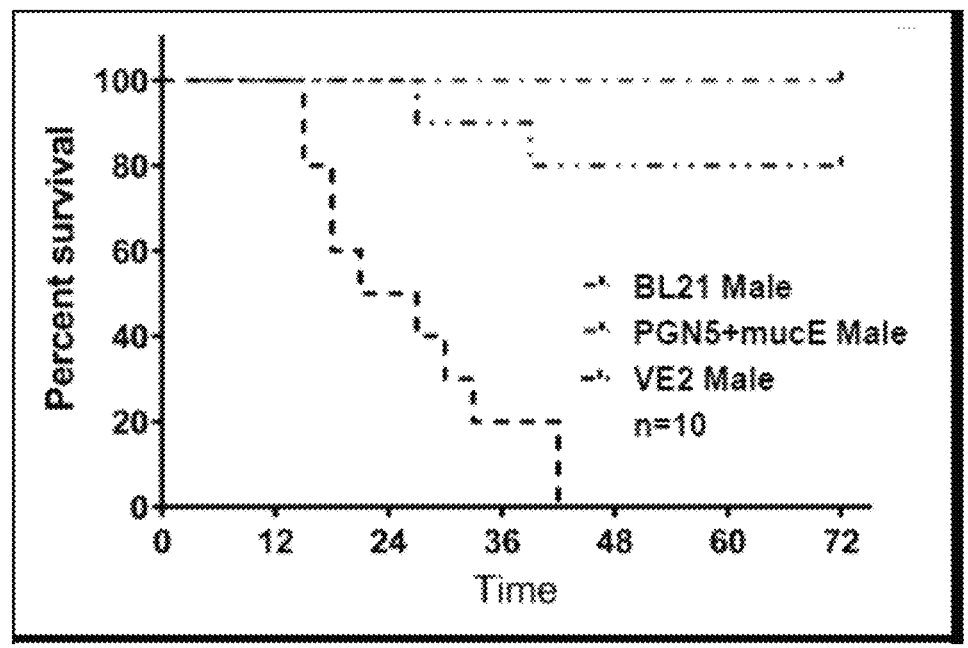
FIGS. 4A-4C include graphs showing percent survival of male and female C57BL/6 mice after injections with *P. aeruginosa* strains VE2, PGN5+mucE, or *E. coli* BL21.
Figure 4B:
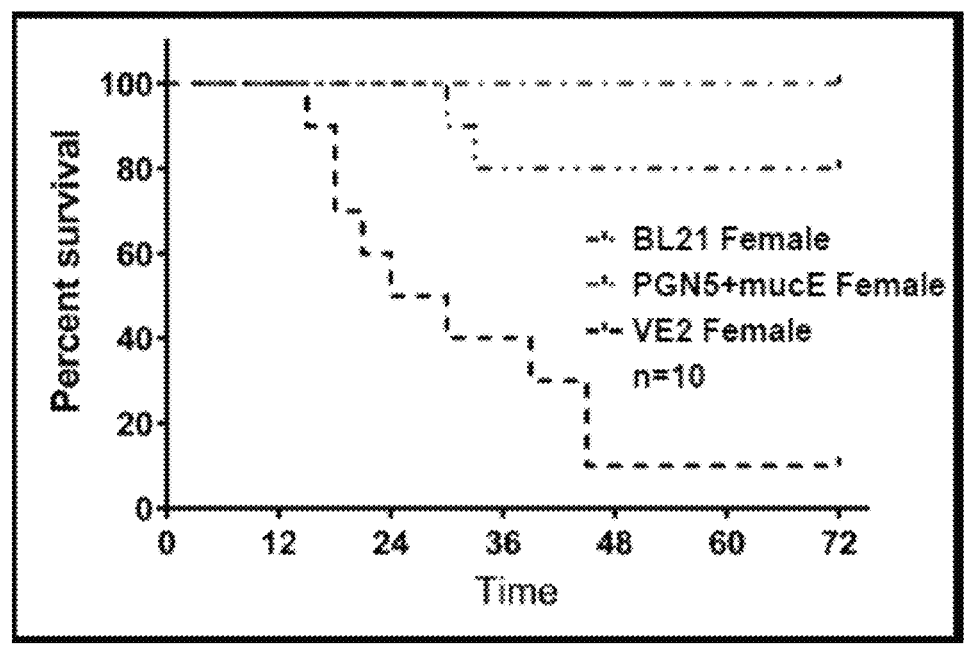
Figure 4C:
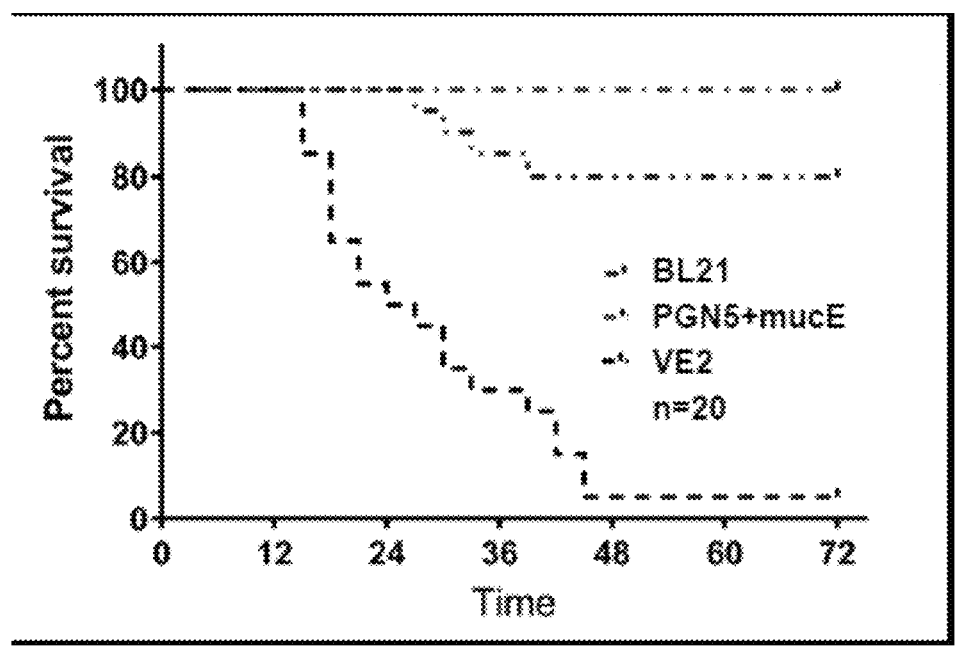

To test whether the pathogenesis of PGN5 was attenuated, C57BL/6 mice were challenged with intraperitoneal injection of $5 \times 10^8$ cells of the PCR- and phenotype-validated strains VE2, PGN5+mucE, or *E. coli* BL21, or PBS as a negative control. Injection with the VE2 strain was fatal in 95% of mice within 48 h (FIGS. 4A-4C). In contrast, injection with BL21 cells resulted in 20% mortality within 48 h, while no mortality was observed from injection with either the PGN5+mucE strain or PBS (FIGS. 4A-4C). The mice were monitored for 4 weeks post-injection, and no change in mortality was observed.

Example 4—a Bioluminescent Construct of PGN5 Did not Disseminate in Mice

Figure 5:
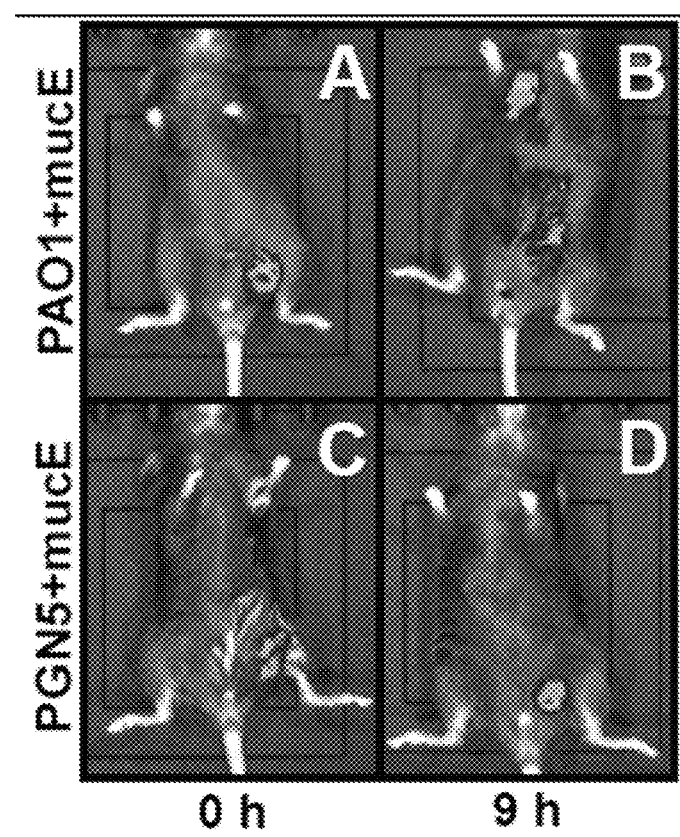
FIG. 5 includes images of mice injected with bioluminescent-labeled *P. aeruginosa* strains. Panels A and B show mice injected with bioluminescent PAO1+mucE at A. 0 h post-injection and B. 9 h post-injection (n=5). Panels C and D show mice injected with bioluminescent PGN5+mucE at (panel C) 0 h post-injection and (panel D) 9 h post-injection (n=5). Different mice were imaged at each time point to avoid overdose of anesthetic.

Since no mortality was observed in mice injected with PGN5+mucE, it was determined whether cells of this strain might localize differently than VE2 cells within the mice post-injection. To test this, the luxCDABEG operon was used to tag each strain with bioluminescence. VE2 and PGN5+mucE both carry gentamicin resistance genes, while the plasmids used for labeling with bioluminescence required gentamicin sensitivity. Thus, the luxCDABEG operon was incorporated into the chromosome of PAO1 and PGN5, and then the pUCP20-pGm-mucE plasmid was introduced into each strain to induce alginate production and mucoidy. Intraperitoneal injection of C57BL/6 mice with bioluminescent PAO1+mucE showed either localization at the injection site or dissemination through the body, and lethality resulted in all mice injected (FIGS. 5A-5B). Conversely, localization at the injection site but no dissemination was observed with bioluminescent PGN5+mucE, and no mortality was observed in injected mice (FIGS. 5C-5D).

Discussion of Examples 1-4

It was previously reported that over-expression of a novel activator of alginate synthesis, MucE, induces high and stable production of alginate in *P. aeruginosa*. In the above-described studies, *P. aeruginosa* strain PGN5 was generated and was engineered by sequentially deleting five pathogenic genes. These gene deletions were verified using multiple DNA sequencing methods and by biochemical or immunological assays to detect the absence or significant reduction of either the gene products or their activity. To test whether the five gene deletions attenuated the virulence of *P. aeruginosa*, mouse infection model studies were performed and the animals were challenged with intraperitoneal injection of mucoid PGN5 (PGN5+mucE), its wild-type counterpart VE2 (PAO1+mucE), or the FDA-approved strain *E. coli* BL21 as a negative control. These strains were validated by PCR, phenotype, and viable plate counts throughout the culture preparation and mouse injection procedure to verify strain authenticity and viable cell number. Inoculation of mice with PGN5 resulted in 0% mortality. In contrast, inoculation with VE2 resulted in 95% mortality while inoculation with BL21 resulted in 20% mortality. These results indicated that PGN5 is a highly attenuated *P. aeruginosa* strain. Indeed, the results indicate that PGN5 is less pathogenic and less toxic than the BL21 *E. coli* strain, which is FDA-approved for production of biopharmaceuticals.

The dissemination of the bacteria was also examined after intraperitoneal injections in the mouse challenge experiments by using bioluminescence-labeled mucoid PAO1 and PGN5 strains. All mice injected with bioluminescent PAO1 succumbed to the infection, while only about 50% exhibited systemic bacterial dissemination. In the other 50%, dissemination of bacterial toxins from the injection site most likely led to septic shock. In contrast, bioluminescent PGN5 was only detected at the injection site, no dissemination was apparent, and zero mortality was observed in these mice. This indicates that the invasiveness and toxin production associated with *P. aeruginosa* is either absent or reduced to a level that does not affect vitality in the PGN5 strain.

Importantly, over-expression of MucE in PGN5 induced stable in vitro production of alginate that was comparable to its wild-type counterpart in chemical structure, physical characteristics of the alginate gel, and total amounts produced. Thus, the genetic modifications in PGN5 have no measurable effect upon the alginate biosynthetic pathway. The viscosities of sodium alginate gels prepared from VE2 and PGN5+mucE alginate were nearly identical, as was the yield stress, suggesting that the gels have similar tensile strength. HPLC chromatograms from alginate produced by VE2 and PGN5 were identical, and rich in M residues. This is consistent with previous reports of bacterial alginates having relatively low G content. While seaweed alginate composition varies between species and plant parts, it generally ranges from about 30-75% G content. In general, alginate with higher G content boasts a higher tensile strength, thus it is a more desirable medium for some medical and industrial applications, such as 3D printing.

Currently, all commercially used alginate has been produced by extraction from brown seaweed. The process of harvesting and extracting alginate from seaweed is labor intensive, requiring harsh acid/base treatments, yielding large amounts of contaminated wastewater. In contrast, bacterial alginate can be extracted from the culture medium via ethanol precipitation, a procedure that does not require treatment with harsh chemicals. Hence, the above-described data indicate that preparing alginate from cultures of PGN5 is a safe and highly reproducible method that is also an environmentally conservative alternative to using seaweed for the commercial production alginate. *P. aeruginosa* is a well-studied microbe, and many tools are available for the genetic manipulation of this organism. This makes PGN5 an attractive option for producing alginates with specific properties for distinct applications, and possibly other recombinant proteins that are difficult to make in *E. coli*. Bioengineering this bacterium can be used to produce alginates with different physical properties, improving upon the characteristics of seaweed alginates and expanding applications for these specialty biopolymers beyond the current uses of alginate.

Example 5—PGN6

Figure 12:
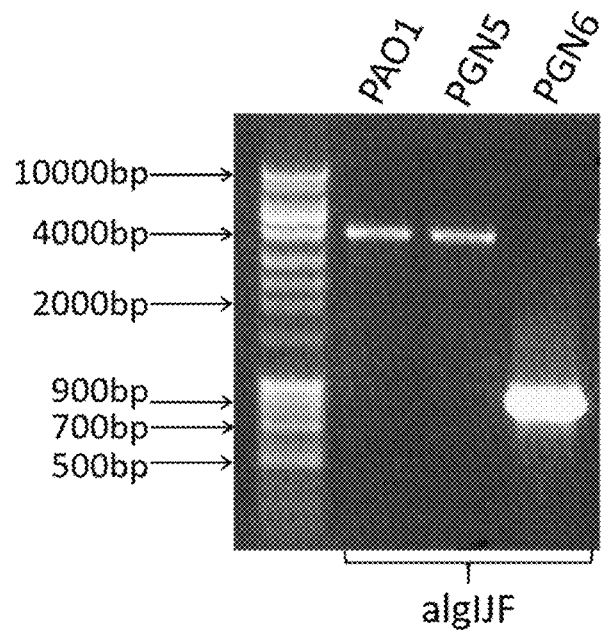
FIG. 12 is an image of a gel showing that PGN6 contains in-frame deletions of the genes encoding the periplasmic proteins algI and algJ. Using the suicide vector pEX100TNotI and two-step allelic exchange, algI and algJ were sequentially deleted from PGN5.

Alginate isolated from brown seaweed is structurally similar to alginate isolated from bacteria of the genera *Azotobacter* and *Pseudomonas*. However, unlike seaweed alginate, bacterial alginates are often acetylated at the C2 and/or C3 positions of D-mannuronate resides. In *P. aeruginosa*, the acetylation of alginate occurs through the combined activity of four genes encoding the periplasmic proteins: AlgI, AlgJ, AlgF, and AlgX. algI, algJ and algF are located sequentially within the alginate biosynthetic operon, separated only by short intergenic genomic DNA sequences, while algX lies further upstream. Deletion of any one of these genes eliminates the ability of the bacterium to acetylate the alginate produced. To generate a marker free, attenuated strain of *P. aeruginosa* that could produce deacetylated alginate identical to seaweed alginate, algI and algJ were deleted in the PGN5 strain using two-step allelic exchange with the *Pseudomonas* gene deletion vector, pEX100TNot1 as described above. The deletion mutant was purified and validated through PCR (FIG. 12), as the mutant had a reduced PCR product relative to the parent. Additionally, the mutant was verified via Sanger sequencing by ligating the product into the pCR4-TOPO vector and sequenced by the WVU Genomics Core Facility with M13F and M13R primers. algI and algJ gene sequences were not detected in the sequencing reactions, while regions directly upstream and downstream of these genes were detected. Thus, in-frame, marker free deletion of algI and algJ was successfully generated.

Example 6—PGN6-polyM

Figure 13:
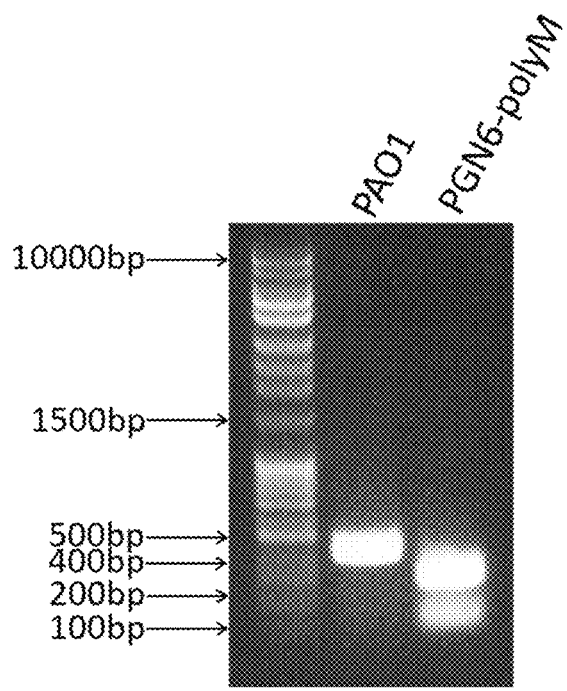
FIG. 13 is an image of a gel showing that PGN6-polyM contains mutations in the algG gene in PGN6 as validated through PCR and HhaI restriction digest.

In *P. aeruginosa*, alginate is polymerized from M monomers, some of which are converted to G residues by the C5-mannuronan epimerase AlgG, yielding an alginate composition of about 30% G and 70% M. Alginates with varying M:G ratios have different properties. For example, alginates with higher G content, especially long stretches of G residues (G-blocks), form stiffer gels. Likewise, alginates with higher M content form more fluid gel structures. By modulating activity of AlgG (or other C5-epimerases), it was believed to be possible to manipulate the M:G composition of alginate. To generate a marker-free, attenuated strain of *P. aeruginosa* that could produce deacetylated alginate, identical to seaweed alginate, and devoid of G residues (polyM), algG was mutated in the PGN6 strain. Deletion of algG eliminated alginate production in *P. aeruginosa*, so two mutations were introduced to the algG gene sequence (A971C, C972G) of the PGN6 strain using the two-step allelic exchange with *Pseudomonas* gene deletion vector, pEX100TNot1, as previously described. The C972G DNA mutation leads to a single amino acid change (D324A) in the active site of AlgG that eliminates its epimerase activity. The A971C mutation is synonymous but generates a recognition site for the restriction enzyme HhaI (recognition site GCGC), which allows for quick screening for mutants with PCR and restriction digest. The deletion mutant was purified and validated through PCR and HhaI restriction digest (FIG. 13) and was also verified via Sanger sequencing by the WVU Genomics Core Facility. The only mutations detected within the algG gene were A971C and C972G.

Example 7—Alginate Production by VE2, PGN5, PGN6, and PGN6-polyM

Figure 14:
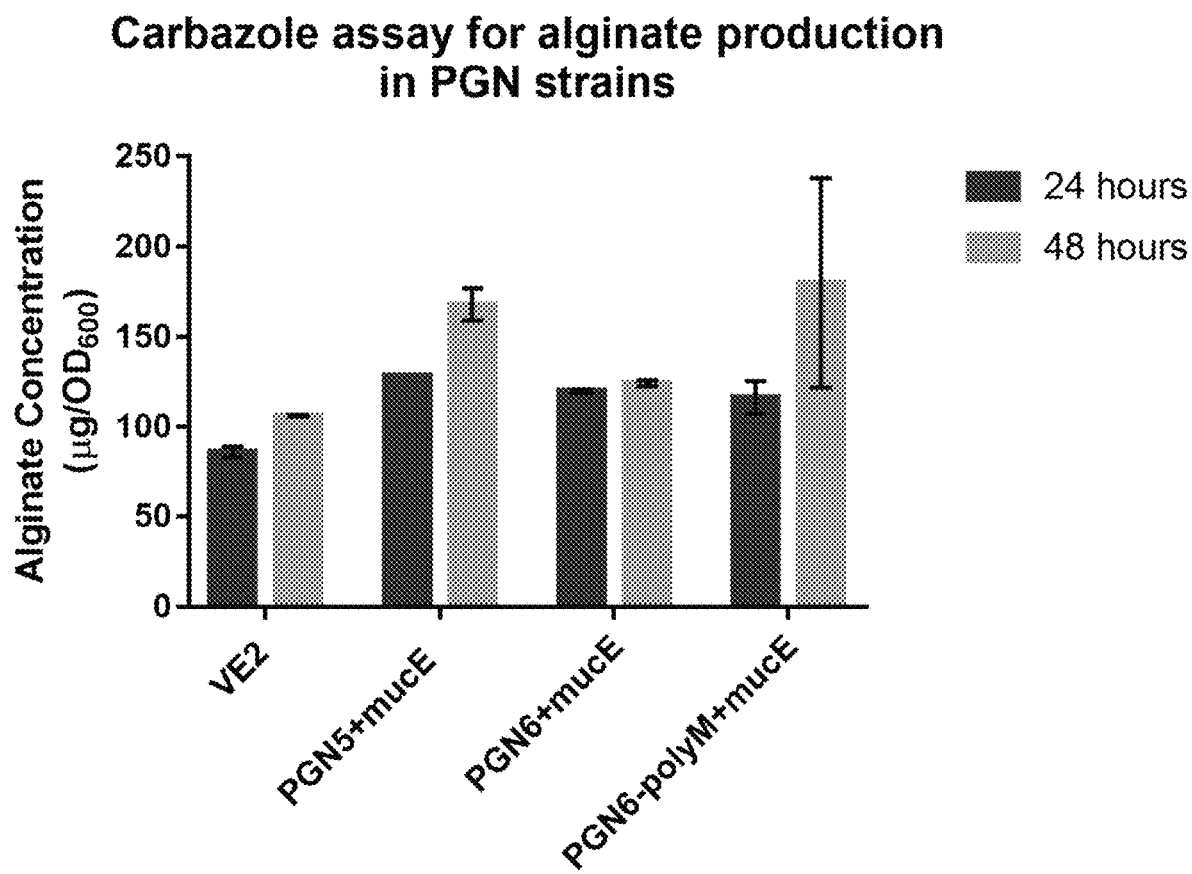
FIG. 14 is a graph showing the results of a carbazole assay utilized to quantify the amount of alginate produced in the *P. aeruginosa* strains VE2, PGN5+mucE, PGN6+mucE, and PGN6-polyM+mucE.

To assess the ability of the newly generated strains to produce alginate, the VE2, PGN5, PGN6, and PGN6-polyM strains were utilized to produce alginate and the alginate production was subsequently measured using a carbazole assay. Briefly, the carbazole assay utilized was a standard uronic acid detection method used to quantify the amount of alginate produced in the *P. aeruginosa* strains VE2, PGN5+mucE, PGN6+mucE, and PGN6-polyM+mucE. Two trials were completed per strain. FIG. 14 shows the average of the two trials +−SD. Each strain was grown on PIA+1 mg/mL aromatic amino acids for 24 h and 48 h at 37° C. Alginate and cells were collected with 0.85% NaCl solution. The number of cells within each cell suspension were determined by measuring the absorbance at 600 nm ($A_{600}$). Cell suspensions were incubated in sulfuric acid/borate solution and carbazole at 55° C. As carbazole reacts with uronic acid, the solution turned a pink to purple color. Absorbance at 530 nm ($A_{530}$) was measured. The concentration of alginate (ug/AU [absorbance unit]) was calculated using a standard curve generated with purified mannuronic alginic acid. As shown in FIG. 14, production of alginate was readily tested and present in each PGN strain upon mucE overexpression as discussed above.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Andersen, T., Strand, B. L., Formo, K., Alsberg, E., and Christensen, B. E. (2012) Alginates as biomaterials in tissue engineering. Carbohydrate Chemistry 37: 227-258.
2. Augst, A. D., Kong, H. J., and Mooney, D. J. (2006) Alginate hydrogels as biomaterials. Macromol Biosci 6(8): 623-633.
3. Bankevich, A., Nurk, S., Antipov, D., Gurevich, A. A., Dvorkin, M., Kulikov, A. S., et al. (2012) SPAdes: A New Genome Assembly Algorithm and Its Applications to Single-Cell Sequencing. Journal of Computational Biology 19(5): 455-477.
4. Blake, M. S., Johnston, K. H., Russell-Jones, G. J., and Gotschlich, E. C. (1984) A rapid, sensitive method for detection of alkaline phosphatase-conjugated anti-antibody on Western blots. Anal Biochem 136(1): 175-179.
5. Choi, K. H., and Schweizer, H. P. (2006) mini-Tn7 insertion in bacteria with single attTn7 sites: example *Pseudomonas aeruginosa*. Nat Protoc 1(1): 153-161.
6. Damron, F. H., Qiu, D., and Yu, H. D. (2009) The *Pseudomonas aeruginosa* sensor kinase KinB negatively controls alginate production through AlgW-dependent MucA proteolysis. J Bacteriol 191(7): 2285-2295.
7. de Kievit, T. R., Dasgupta, T., Schweizer, H., and Lam, J. S. (1995) Molecular cloning and characterization of the rfc gene of *Pseudomonas aeruginosa* (serotype 05). Mol Microbiol 16(3): 565-574.
8. Draget, K. I., SmidsrøO., and Skjåk-Bræk, G. (2005) Alginates from Algae. Biopolymers Online. A. Steinbüchel, Wiley-VCH Verlag GmbH & Co. KGaA
9. Driscoll, J. A., Brody, S. L., and Kollef, M. H. (2007) The epidemiology, pathogenesis and treatment of *Pseudomonas aeruginosa* infections. Drugs 67(3): 351-368.
10. Essar, D. W., Eberly, L., Hadero, A., and Crawford, I. P. (1990) Identification and characterization of genes for a second anthranilate synthase in *Pseudomonas aeruginosa*: interchangeability of the two anthranilate synthases and evolutionary implications. J Bacteriol 172(2): 884-900.
11. Fertah, M., Belfkira, A., Dahmane, E. m., Taourirte, M., and Brouillette, F. (2017) Extraction and characterization of sodium alginate from Moroccan Laminaria digitata brown seaweed. Arabian Journal of Chemistry 10: S3707-S3714.
12. Figurski, D. H., and Helinski, D. R. (1979) Replication of an origin-containing derivative of plasmid RK2 dependent on a plasmid function provided in trans. Proc Natl Acad Sci U S A 76(4): 1648-1652.
13. Fomsgaard, A., Freudenberg, M. A., and Galanos, C. (1990) Modification of the silver staining technique to detect lipopolysaccharide in polyacrylamide gels. J Clin Microbiol 28(12): 2627-2631.
14. Gellatly, S. L., and Hancock, R. E. (2013) *Pseudomonas aeruginosa*: new insights into pathogenesis and host defenses. Pathog Dis 67(3): 159-173.
15. Gorin, P. A. J., and Spencer, J. F. T. (1966) Exocellular alginic acid from *Azotobacter* vinelandii. Canadian Journal of Chemistry 44(9): 993-998.
16. Govan, J. R., and Fyfe, J. A. (1978) Mucoid *Pseudomonas aeruginosa* and cystic fibrosis: resistance of the mucoid form to carbenicillin, flucloxacillin and tobramycin and the isolation of mucoid variants in vitro. Journal of Antimicrobial Chemotherapy 4(3): 233-240.
17. Govan, J. R., Fyfe, J. A., and Jarman, T. R. (1981) Isolation of alginate-producing mutants of *Pseudomonas fluorescens*, *Pseudomonas* putida and *Pseudomonas* mendocina. J Gen Microbiol 125(1): 217-220.
18. Haug, A., Larsen, B., and Smidsrø O. (1966) A study on the constitution of alginic acid by partial acid hydrolysis. Acta chemica Scandinavica 20: 271-277.
19. Helgerud, T., Gåserø O., Fjæreide, T., Andersen, P. O., and Larsen, C. K. (2009) Alginates. Food stabilisers, thickeners and gelling agents. A. Imeson. Oxford, Wiley-Blackwell: 50-72.
20. Hitchcock, P. J., and Brown, T. M. (1983) Morphological heterogeneity among Salmonella lipopolysaccharide chemotypes in silver-stained polyacrylamide gels. J Bacteriol 154(1): 269-277.
21. Iglewski, B. H., Liu, P. V., and Kabat, D. (1977) Mechanism of action of *Pseudomonas aeruginosa* exotoxin Aiadenosine diphosphate-ribosylation of mammalian elongation factor 2 in vitro and in vivo. Infect Immun 15(1): 138-144.
22. Kropinski, A. M., Chan, L. C., and Milazzo, F. H. (1979) The extraction and analysis of lipopolysaccharides from *Pseudomonas aeruginosa* strain PAO, and three rough mutants. Can J Microbiol 25(3): 390-398.
23. Langmead, B., and Salzberg, S. L. (2012) Fast gapped-read alignment with Bowtie 2. Nature Methods 9: 357.
24. Lee, K. Y., and Mooney, D. J. (2012) Alginate: properties and biomedical applications. Prog Polym Sci 37(1): 106-126.
25. Leid, J. G., Willson, C. J., Shirtliff, M. E., Hassett, D. J., Parsek, M. R., and Jeffers, A. K. (2005) The exopolysaccharide alginate protects *Pseudomonas aeruginosa* biofilm bacteria from IFN-gamma-mediated macrophage killing. J Immunol 175(11): 7512-7518.
26. Li, P., Lo, C. C., Davenport, K., and Chain, P. (2018) PanGIA: A Metagenomics Analytical Framework for Routine Biosurveillance in the Clinic and Beyond. In Preparation.
27. Linker, A., and Jones, R. S. (1966) A new polysaccharide resembling alginic acid isolated from pseudomonads. J Biol Chem 241(16): 3845-3851.
28. Liu, F., Wang, X., Shi, H., Wang, Y., Xue, C., and Tang, Q. J. (2017) Polymannuronic acid ameliorated obesity and inflammation associated with a high-fat and high-sucrose diet by modulating the gut microbiome in a murine model. Br J Nutr 117(9): 1332-1342.
29. Liu, P. V. (1966) The roles of various fractions of *Pseudomonas aeruginosa* in its pathogenesis. 3. Identity of the lethal toxins produced in vitro and in vivo. J Infect Dis 116(4): 481-489.
30. Lyczak, J. B., Cannon, C. L., and Pier, G. B. (2002) Lung infections associated with cystic fibrosis. Clin Microbiol Rev 15(2): 194-222.
31. Michalska, M., and Wolf, P. (2015) *Pseudomonas* Exotoxin A: optimized by evolution for effective killing. Front Microbiol 6: 963.
32. Moradali, M. F., Donati, I., Sims, I. M., Ghods, S., and Rehm, B. H. (2015) Alginate Polymerization and Modification Are Linked in *Pseudomonas aeruginosa*. MBio 6(3): e00453-00415.
33. Mortazavi-Jahromi, S. S., Alizadeh, S., Javanbakht, M. H., and Mirshafiey, A. (2018) Anti-diabetic effect of beta-D-mannuronic acid (M2000) as a novel NSAID with immunosuppressive property on insulin production, blood glucose, and inflammatory markers in the experimental diabetes model. Arch Physiol Biochem: 1-6.
34. Nivens, D. E., Ohman, D. E., Williams, J., and Franklin, M. J. (2001) Role of alginate and its O acetylation in formation of *Pseudomonas aeruginosa* microcolonies and biofilms. J Bacteriol 183(3): 1047-1057.
35. Paul, W., and Sharma, C. P. (2004) Chitosan and alginate wound dressings: a short review. Trends in Biomaterials and Artificial Organs 18(1): 18-23.
36. Pedersen, S. S., Kharazmi, A., Espersen, F., and Hoiby, N. (1990) *Pseudomonas aeruginosa* alginate in cystic fibrosis sputum and the inflammatory response. Infect Immun 58(10): 3363-3368.
37. Peteiro, C. (2018) Alginate Production from Marine Macroalgae, with Emphasis on Kelp Farming. Alginates and Their Biomedical Applications. Springer Series in Biomaterials Science and Engineering. B. Rehm and M. Moradali. Singapore, Springer. 11.
38. Pier, G. B., Coleman, F., Grout, M., Franklin, M., and Ohman, D. E. (2001) Role of alginate O acetylation in resistance of mucoid *Pseudomonas aeruginosa* to opsonic phagocytosis. Infect Immun 69(3): 1895-1901.
39. Priebe, G. P., Brinig, M. M., Hatano, K., Grout, M., Coleman, F. T., Pier, G. B., and Goldberg, J. B. (2002) Construction and characterization of a live, attenuated aroA deletion mutant of *Pseudomonas aeruginosa* as a candidate intranasal vaccine. Infect Immun 70(3): 1507-1517.
40. Qiu, D., Eisinger, V. M., Rowen, D. W., and Yu, H. D. (2007) Regulated proteolysis controls mucoid conversion in *Pseudomonas aeruginosa*. Proc Natl Acad Sci U S A 104(19): 8107-8112.
41. Qu, Y., Wang, Z., Zhou, H., Kang, M., Dong, R., and Zhao, J. (2017) Oligosaccharide nanomedicine of alginate sodium improves therapeutic results of posterior lumbar interbody fusion with cages for degenerative lumbar disease in osteoporosis patients by downregulating serum miR-155. International Journal of Nanomedicine 12(1): 8459-8469.
42. Rada, B., and Leto, T. L. (2013) Pyocyanin effects on respiratory epithelium: relevance in *Pseudomonas aeruginosa* airway infections. Trends Microbiol 21(2): 73-81.
43. Rocchetta, H. L., Burrows, L. L., Pacan, J. C., and Lam, J. S. (1998) Three rhamnosyltransferases responsible for assembly of the A-band D-rhamnan polysaccharide in *Pseudomonas aeruginosa*: a fourth transferase, WbpL, is required for the initiation of both A-band and B-band lipopolysaccharide synthesis. Mol Microbiol 28(6): 1103-1119.
44. Schwarzmann, S., and Boring, J. R. (1971) Antiphagocytic Effect of Slime from a Mucoid Strain of *Pseudomonas aeruginosa*. Infect Immun 3(6): 762-767.

45. Schweizer, H. P., and Hoang, T. T. (1995) An improved system for gene replacement and xylE fusion analysis in *Pseudomonas aeruginosa*. Gene 158(1): 15-22.
46. Seemann, T. (2014) Prokka: rapid prokaryotic genome annotation. Bioinformatics 30(14): 2068-2069.
47. SmithsrøO., and Whittington, S. G. (1969) Monte Carlo investigation of chemical inhomogeneity in copolymers. Macromolecules 2(1): 42-44.
48. Stokke, B. T., SmidsrøO., and Brant, D. A. (1993) Predicted influence of monomer sequence distribution and acetylation on the extension of naturally occurring alginates. Carbohydrate Polymers 22(1): 57-66.
49. Taeb, M., Jafarzadeh, A., Mortazavi-Jahromi, S. S., Zainodini, N., Mirzaei, M. R., Jafarnezhad-Ansariha, F., et al. (2018) Effect of beta-D-mannuronic acid (M2000) on oxidative stress enzymes' gene using healthy donor peripheral blood mononuclear cells for evaluating the anti-aging property. Curr Drug Discov Technol.
50. Tatnell, P. J., Russell, N. J., Govan, J. R., and Gacesa, P. (1996) Characterisation of alginates from mucoid strains of *Pseudomonas aeruginosa*. Biochem Soc Trans 24(3): 404S.
51. Vold, I. M., Kristiansen, K. A., and Christensen, B. E. (2006) A study of the chain stiffness and extension of alginates, in vitro epimerized alginates, and periodate-oxidized alginates using size-exclusion chromatography combined with light scattering and viscosity detectors. Biomacromolecules 7(7): 2136-2146.
52. Winsor, G. L., Griffiths, E. J., Lo, R., Dhillon, B. K., Shay, J. A., and Brinkman, F. S. (2016) Enhanced annotations and features for comparing thousands of *Pseudomonas* genomes in the *Pseudomonas* genome database. Nucleic Acids Res 44(D1): D646-653.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A bacterial culture, comprising a modified *Pseudomonas aeruginosa* bacterium missing or deficient in a plurality of virulence factors, the plurality of virulence factors comprising exotoxin A, hemolytic phospholipase C, phenazine-specific methyltransferase, and alpha-1,3-rhamnosyltransferase.

2. The bacterial culture of claim 1, wherein the modified *Pseudomonas aeruginosa* bacterium includes a deletion of a plurality of virulence factor genes, the plurality of virulence factor genes comprising an exotoxin A gene (toxA), a hemolytic phospholipase C gene (plcH), a phenazine specific methyltransferase gene (phzM), and an alpha-1,3-rhamnosyltransferase gene (wapR).

3. The bacterial culture claim 1, wherein the modified *Pseudomonas aeruginosa* bacterium is further missing or deficient in one or more alginate acetylation enzymes, the one or more alginate acetylation enzymes selected from the group consisting of alginate O-acetyltransferase AlgI, alginate O-acetyltransferase AlgJ, alginate O-acetyltransferase AlgF, and alginate O-acetyltransferase AlgX.

4. The bacterial culture of claim 3, wherein the modified *Pseudomonas aeruginosa* bacterium is missing or deficient in alginate O-acetyltransferase AlgI and alginate O-acetyltransferase AlgJ.

5. The bacterial culture of claim 3, wherein the modified *Pseudomonas aeruginosa* bacterium includes a deletion of one or more alginate acetylation genes, the alginate acetylation genes selected from the group consisting of algI, algJ, algF, and algX.

6. The bacterial culture of claim 1, wherein the modified *Pseudomonas aeruginosa* bacterium further includes an algG gene having one or more mutations, and wherein the algG gene encodes an AlgG polypeptide having decreased C5-mannuronan epimerase activity as compared to wild-type *Pseudomonas aeruginosa* bacteria.

7. A modified *Pseudomonas aeruginosa* bacterium missing or deficient in a plurality of virulence factors, the plurality of virulence factors comprising exotoxin A, hemolytic phospholipase C, phenazine-specific methyltransferase, and alpha-1,3-rhamnosyltransferase.

8. The modified *Pseudomonas aeruginosa* bacterium of claim 7, wherein the modified *Pseudomonas aeruginosa* bacterium is further missing or deficient in alginate O-acetyltransferase AlgI and alginate O-acetyltransferase AlgJ.

9. The modified *Pseudomonas aeruginosa* bacterium of claim 8, wherein the modified *Pseudomonas aeruginosa* bacterium includes an algG gene having one or more mutations, and wherein the algG gene encodes an AlgG having decreased C5-mannuronan epimerase activity as compared to wild-type *Pseudomonas aeruginosa* bacteria.

10. The modified *Pseudomonas aeruginosa* bacterium of claim 7, wherein the modified *Pseudomonas aeruginosa* bacterium is non-pathogenic.

11. A method of producing alginate, comprising culturing a modified *Pseudomonas aeruginosa* bacterium missing or deficient in a plurality of virulence factors, the plurality of virulence factors comprising exotoxin A, hemolytic phospholipase C, phenazine-specific methyltransferase, and alpha-1,3-rhamnosyltransferase.

12. The method of claim 11, wherein the modified *Pseudomonas aeruginosa* bacterium is transformed with a vector encoding a MucE polypeptide, and wherein the MucE polypeptide is expressed in the bacterium subsequent to transformation with the vector.

13. The method of claim 11, further comprising isolating the alginate produced by the modified *Pseudomonas aeruginosa* bacterium.

14. The method of claim 11, wherein the modified *Pseudomonas aeruginosa* bacterium is missing or deficient in one or more alginate acetylation enzymes selected from the group consisting of alginate O-acetyltransferase AlgI, alginate O-acetyltransferase AlgJ, alginate O-acetyltransferase AlgF, and alginate O-acetyltransferase AlgX.

15. The method of claim 14, wherein the alginate produced by the modified *Pseudomonas aeruginosa* bacterium is non-acetylated.

16. The method of claim 14, wherein the modified *Pseudomonas aeruginosa* bacterium is missing or deficient in alginate O-acetyltransferase AlgI and alginate O-acetyltransferase AlgJ.

17. The method of claim 11, wherein the modified *Pseudomonas aeruginosa* bacterium includes an algG gene having one or more mutations, and wherein the algG gene encodes an AlgG polypeptide having decreased C5-mannuronan epimerase activity as compared to wild-type *Pseudomonas aeruginosa* bacteria.

* * * * *